United States Patent
Piotrowski

(10) Patent No.: US 6,818,641 B2
(45) Date of Patent: Nov. 16, 2004

(54) ARTHROPODICIDAL CARBOXANILIDES

(75) Inventor: David Walter Piotrowski, Portage, MI (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 10/220,446

(22) PCT Filed: Mar. 26, 2001

(86) PCT No.: PCT/US01/09716

§ 371 (c)(1),
(2), (4) Date: Aug. 28, 2002

(87) PCT Pub. No.: WO01/72696

PCT Pub. Date: Oct. 4, 2001

(65) Prior Publication Data

US 2003/0139397 A1 Jul. 24, 2003

Related U.S. Application Data

(60) Provisional application No. 60/192,825, filed on Mar. 29, 2000.

(51) Int. Cl.[7] .................... C07D 253/06; C07D 253/10; C07D 487/04; C07D 491/04; A01N 43/707
(52) U.S. Cl. .................. 514/242; 514/243; 544/182; 544/183; 544/184
(58) Field of Search .............................. 544/182, 183, 544/184; 514/242, 243

(56) References Cited

U.S. PATENT DOCUMENTS 5,462,938 A   10/1995   Annus et al.

FOREIGN PATENT DOCUMENTS

| WO | WO 9117983 | 11/1991 |
|----|------------|---------|
| WO | WO 9220682 | 11/1992 |
| WO | WO 9319045 | 9/1993  |

*Primary Examiner*—Venkataraman Balasubramanian

(57) ABSTRACT

Compounds of Formula (I), and their N-oxides and agriculturally suitable salts, are disclosed which are useful as arthropodicides wherein A is H; E is H or $C_1-C_3$ alkyl; or A and E can be taken together to form —$CH_2$—, —$CH_2CH_2$—, —O—, —S—, —S(O)—, —S(O)$_2$—, —$NR^8$—, —$OCH_2$—, —$SCH_2$—, —$N(R^8)CH_2$—, substituted —$CH_2$— and substituted —$CH_2CH_2$—, the substituents independently selected from 1-2 halogen and 1-2 methyl; W is N or $CR^4$; X is $CR^5R^6$, O, S, $NR^7$ or a direct bond, provided that when W is N, then X is other than a direct bond; Y is H, $C_1-C_6$ alkyl, $C_2-C_6$ alkenyl, $C_2-C_6$ alkynyl, $C_1-C_3$ alkylsulfonyl, $C_3-C_6$ cycloalkyl, $C_3-C_6$ cycloalkylalkyl, $NR^9R^{10}$, $N=CR^{11}R^{12}$, $OR^7$, $COR^{13}$, $CO_2R^{14}$ or $C_1-C_6$ alkyl substituted by at least one group selected from halogen, $C_1-C_3$ alkoxy, CN, $NO_2$, $S(O)_rR^{15}$, $COR^{13}$, $CO_2R^{14}$ and optionally substituted phenyl; Z is O or S; and $R^2, R^3, R^4, R^5, R^6, R^7, R^8, R^9, R^{10}, R^{11}, R^{12}, R^{13}, R^{14}, R^{15}$, G, n and r are as defined in the disclosure. Also disclosed are compositions containing the compounds of Formula (I) and a method for controlling arthropods which involves contacting the arthropods or their environment with an effective amount of a compound of Formula (I).

5 Claims, No Drawings

ARTHROPODICIDAL CARBOXANILIDES

BACKGROUND OF THE INVENTION

This invention relate's to certain carboxanilides, their N-oxides, agriculturally suitable salts and compositions, and methods of their use as arthropodicides in both agronomic and nonagronomic environments.

The control of arthropod pests is extremely important in achieving high crop efficiency. Arthropod damage to growing and stored agronomic crops can cause significant reduction in productivity and thereby result in increased costs to the consumer. The control of arthropod pests in forestry, greenhouse crops, ornamentals, nursery crops, stored food and fiber products, livestock, household, and public and animal health is also important. Many products are commercially available for these purposes, but the need continues for new compounds which are more effective, less costly, less toxic, environmentally safer or have different modes of action.

SUMMARY OF THE INVENTION

This invention is directed to compounds of Formula I including all geometric and stereoisomers, N-oxides, and agriculturally suitable salts thereof, agricultural compositions containing them and their use to control arthropods in agronomic and nonagronomic environments

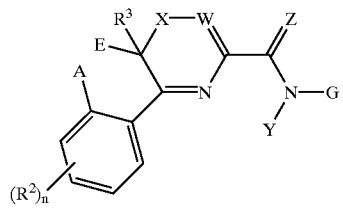

I wherein:

A is H;

E is H or $C_1$–$C_3$ alkyl; or

A and E can be taken together to form —$CH_2$—, —$CH_2CH_2$—, —O—, —S—, —S(O)—, —$S(O)_2$—, —$NR^8$—, —$OCH_2$—, —$SCH_2$—, —$N(R^8)CH_2$—, substituted —$CH_2$— and substituted —$CH_2CH_2$—, the substituents on each carbon independently selected from 1-2 halogen and 1-2 methyl;

G is selected from the group consisting of

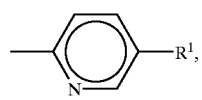 G-1

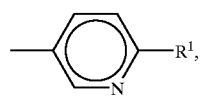 G-2

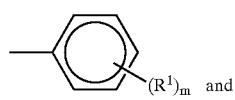 G-3 and

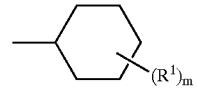 G-4

W is N or $CR^4$;

X is $CR^5R^6$, O, S, $NR^7$ or a direct bond, provided that when W is N, then X is other than a direct bond;

Y is H, $C_1$–$C_6$ alkyl, $C_2$–$C_6$ alkenyl, $C_2$–$C_6$ alkynyl, $C_1$–$C_3$ alkylsulfonyl, $C_3$–$C_6$ cycloalkyl, $C_3$–$C_6$ cycloalkylalkyl, $NR^9R^{10}$, $N=CR^{11}R^{12}$, $OR^7$, $COR^{13}$, $CO_2R^{14}$ or $C_1$–$C_6$ alkyl substituted by at least one group selected from halogen, $C_1$–$C_3$ alkoxy, CN, $NO_2$, $S(O)_rR^{15}$, $COR^{13}$, $CO_2R^{14}$ and optionally substituted phenyl;

Z is O or S;

each $R^1$ and $R^2$ is independently selected from the group consisting of $C_1$–$C_6$ haloalkyl, $C_2$–$C_6$ haloalkenyl, halogen, CN, $NO_2$, $OR^{16}$, $S(O)_rR^{15}$, $OS(O)_2R^{15}$, $CO_2R^{14}$, $C(O)R^{13}$, $C(O)NR^9R^{10}$, $SO_2NR^9R^{10}$, $SF_5$, optionally substituted phenyl and optionally substituted benzyl; or when m or n is 2, $(R^1)_2$ can be taken together or $(R^2)_2$ can be taken together as —$OCH_2O$—, —$OCF_2O$—, —$OCH_2CH_2O$—, —$CH_2C(CH_3)_2O$—, —$CF_2CF_2O$ or —$OCF_2CF_2O$—;

$R^3$ is selected from the group consisting of J, $C(R^{17})=N$—$O$—$R^{18}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxylalkyl, $C_3$–$C_8$ alkoxycarbonylalkyl, $CO_2R^{14}$, $C(O)R^{13}$, $C(O)NR^9R^{10}$, $C(S)NR^9R^{10}$, $C(S)R^{13}$, $C(S)SR^{13}$, CN, and optionally substituted phenyl; or $R^3$ is $C_2$–$C_6$ epoxyalkyl optionally substituted with a group selected from $C_1$–$C_3$ alkyl, CN, $C(O)R^{13}$, $CO_2R^{14}$ and optionally substituted phenyl; or $R^3$ is $C_1$–$C_6$ alkyl substituted with a group selected from $C(O)NR^9R^{10}$, $COR^{13}$, $CO_2R^{14}$, $S(O)_mR^{15}$, SCN, CN, $C_1$–$C_2$ haloalkoxy, $SiR^{19}R^{20}R^{21}$, $NR^9R^{10}$, $NO_2$, $OC(O)R^{13}$, —$P(O)(OR^{22})_2$, optionally substituted phenyl, and J;

J is a nonaromatic or aromatic 5- or 6-membered heterocyclic ring, bonded through carbon or nitrogen, containing 1-4 heteroatoms independently selected from the group consisting of 0-2 oxygen, 0-2 sulfur and 0-4 nitrogen, optionally containing one carbonyl moiety and optionally substituted;

$R^4$, $R^5$ and $R^6$ are each independently H or $C_1$–$C_4$ alkyl;

each $R^7$ is independently H, $C_1$–$C_4$ alkyl, $C_1$–$C_4$ haloalkyl, $C_2$–$C_4$ alkenyl, $C_2$–$C_4$ alkynyl, $C_1$–$C_4$ alkoxy, $SO_2NR^9R^{10}$, $SO_2R^{13}$, $COR^9$, $CONR^9R^{10}$, $CO_2R^{13}$, optionally substituted phenyl or optionally substituted benzyl;

each $R^8$ is independently H, $C_1$–$C_4$ alkyl, $C_1$–$C_4$ alkoxyalkyl, $CO_2R^{13}$, $SO_2R^{13}$, or optionally substituted benzyl;

each $R^9$ and each $R^{11}$ is independently H, $C_1$–$C_4$ alkyl, $C_1$–$C_4$ haloalkyl or optionally substituted phenyl;

each $R^{10}$ and each $R^{12}$ is independently H or $C_1$–$C_4$ alkyl; or each pair of $R^9$ and $R^{10}$ when attached to the same atom or each pair of $R^{11}$ and $R^{12}$ when attached to the same atom independently can be taken together as —$CH_2CH_2CH_2$—, —$CH_2CH_2CH_2CH_2$—, —$CH_2CH_2CH_2CH_2CH_2$— or —$CH_2CH_2OCH_2CH_2$—, each of which is optionally and independently substituted with 1 or 2 $CH_3$ groups;

each $R^{13}$ and each $R^{15}$ is independently H, $C_1-C_4$ alkyl, $C_1-C_4$ haloalkyl or optionally substituted phenyl;

each $R^{14}$ is independently H, $C_1-C_4$ alkyl, $C_1-C_4$ haloalkyl or optionally substituted benzyl;

$R^{16}$ is H, $C_1-C_6$ alkyl, $C_1-C_6$ haloalkyl, $C_2-C_6$ alkenyl, $C_2-C_6$ haloalkenyl, $C_2-C_6$ alkynyl, $C_3-C_6$ haloalkynyl, $C_2-C_6$ alkoxyalkyl, $C_2-C_6$ alkylthioalkyl, $C_1-C_6$ nitroalkyl, $C_2-C_6$ cyanoalkyl, $C_3-C_8$ alkoxycarbonylalkyl, $C_3-C_6$ cycloalkyl, $C_3-C_6$ halocycloalkyl, optionally substituted phenyl and optionally substituted benzyl;

$R^{17}$ is selected from the group consisting of H, Cl, $C_1-C_4$ alkyl, $C_1-C_4$ alkoxy, $C_1-C_2$ thioalkyl and CN;

$R^{18}$ is selected from the group consisting of H, $C_1-C_4$ alkyl, $C_2-C_3$ alkylcarbonyl and $C_2-C_3$ alkoxycarbonyl;

$R^{19}$ and $R^{20}$ are each independently $C_1-C_3$ alkyl;

$R^{21}$ is selected from the group consisting of H, $C_1-C_3$ alkyl and optionally substituted phenyl;

each $R^{22}$ is independently H or $C_1-C_4$ alkyl;

each m and n are independently 1 to 3; and r is 0, 1 or 2.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfinyl isomers. "Cyanoalkyl" denotes an alkyl group substituted with one cyano group. Examples of "cyanoalkyl" include $NCCH_2$, $NCCH_2CH_2$ and $CH_3CH(CN)CH_2$. "Cycloalkyl" includes, for example, cyclopropyl, cyclobutyl, cyclopentyl, and cyclohexyl. Examples of "cycloalkylalkyl" include cyclopropylmethyl, cyclopentylethyl, and other cycloalkyl moieties bonded to straight-chain or branched alkyl groups. Examples of "cycloalkylalkoxy" include cyclopropylmethoxy, cyclopentylethoxy, and other cycloalkyl moieties bonded to straight-chain or branched alkoxy groups. Examples of "alkylcarbonyl" include $C(O)CH_3$, $C(O)CH_2CH_2CH_3$ and $C(O)CH(CH_3)_2$. Examples of "allcoxycarbonyl" include $CH_3OC(=O)$, $CH_3CH_2OC(=O)$, $CH_3CH_2CH_2OC(=O)$, $(CH_3)_2CHOC(=O)$ and different butoxy- or pentoxycarbonyl isomers. Examples of "alkoxycarbonylalkyl" include $CH_3OC(=O)CH_2$, $CH_3CH_2OC(=O)CH_2$, $CH_3OC(=O)CH_2CH_2$, $CH_3CHOC(=O)CH_2CH_2$ and the different propoxy-, butoxy- or pentoxycarbonyl isomers.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$.

The term "aromatic ring" denotes fully unsaturated carbocycles and heterocycles in which the ring is aromatic (where aromatic indicates that the Hückel rule is satisfied for the ring system). The term "aromatic heterocyclic ring" includes fully aromatic heterocycles (where aromatic indicates that the Hückel rule is satisfied). The term "nonaromatic heterocyclic ring" denotes fully saturated heterocycles as well as partially or fully unsaturated heterocycles where the Hückel rule is not satisfied. The heterocyclic ring systems can be attached through any available carbon or nitrogen by replacement of a hydrogen on said carbon or nitrogen. The term "benzyl" denotes a —$CH_2C_6H_5$ moiety in which the $C_6H_5$ ring is aromatic.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^4$ or $R^7$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

In Formula I, the term "optionally substituted" in reference to certain phenyl, benzyl or J rings (see the definitions of Y, J, $R^1$, $R^2$, $R^3$, $R^7$, $R^8$, $R^9$, $R^{11}$, $R^{13}$, $R^{14}$, $R^{15}$, $R^{16}$ and $R^{21}$) refers to a phenyl, benzyl or J ring that is unsubstituted, or is substituted with at least one non-hydrogen group that does not extinguish the arthropodicidal activity possessed by the analog in which the phenyl, benzyl or J ring is unsubstituted. In the case of a phenyl ring or a benzyl ring, the optional non-hydrogen group is attached to a carbon atom contained within the aromatic ring. In the case of J, a nonaromatic or aromatic 5- or 6-membered heterocyclic ring, bonded through carbon or nitrogen, containing 1-4 heteroatoms independently selected from the group consisting of 0-2 oxygen, 0-2 sulfur and 0-4 nitrogen, optionally containing one carbonyl moiety and optionally substituted, the optional non-hydrogen group is attached to either a carbon atom or a nitrogen within the ring. Examples of optionally substituted phenyl, benzyl or J rings are those wherein said rings are optionally substituted with $R^{23}$ and optionally substituted with $R^{24}$, wherein each $R^{23}$ is independently selected from the group consisting of 1-2 halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl; and each $R^{24}$ is independently selected from the group consisting of halogen, $C_1$–$C_4$ alkyl, $C_1$–$C_4$ alkoxy, $C_1$–$C_4$ haloalkyl and $C_1$–$C_4$ haloalkoxy.

Examples of phenyl, benzyl or J rings wherein said rings are optionally substituted with $R^{23}$ and/or $R^{24}$ include the rings illustrated in Exhibit 1 as a phenyl ring optionally substituted with $R^{23}$ and/or $R^{24}$, a benzyl ring optionally substituted with $R^{23}$ and/or $R^{24}$, 5- or 6-membered aromatic heterocyclic rings (J-1 to J-28), and 5- or 6-membered nonaromatic heterocyclic rings optionally containing one carbonyl moiety (J-29 to J-50). As with the carbon atoms in the ring, the nitrogen atoms that require substitution to fill their valence are substituted with hydrogen or with $R^{23}$ and/or $R^{24}$. Although the $R^{23}$ and/or $R^{24}$ groups are shown in the structures illustrated in Exhibit 1, it is noted that $R^{23}$ and/or $R^{24}$ do not need to be present since they are optional substituents.

Exhibit 1

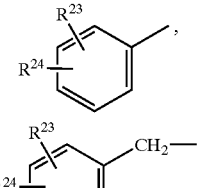

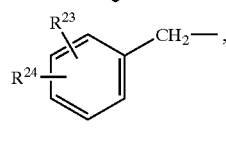

J-1

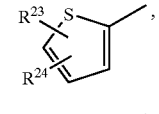

J-2

J-3

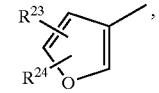

J-4

J-5

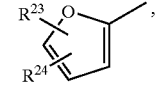

J-6

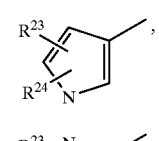

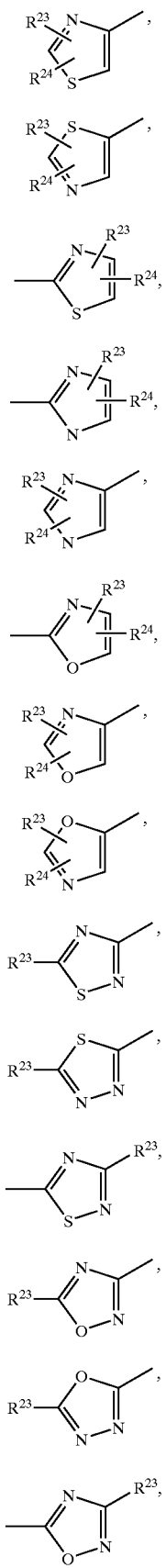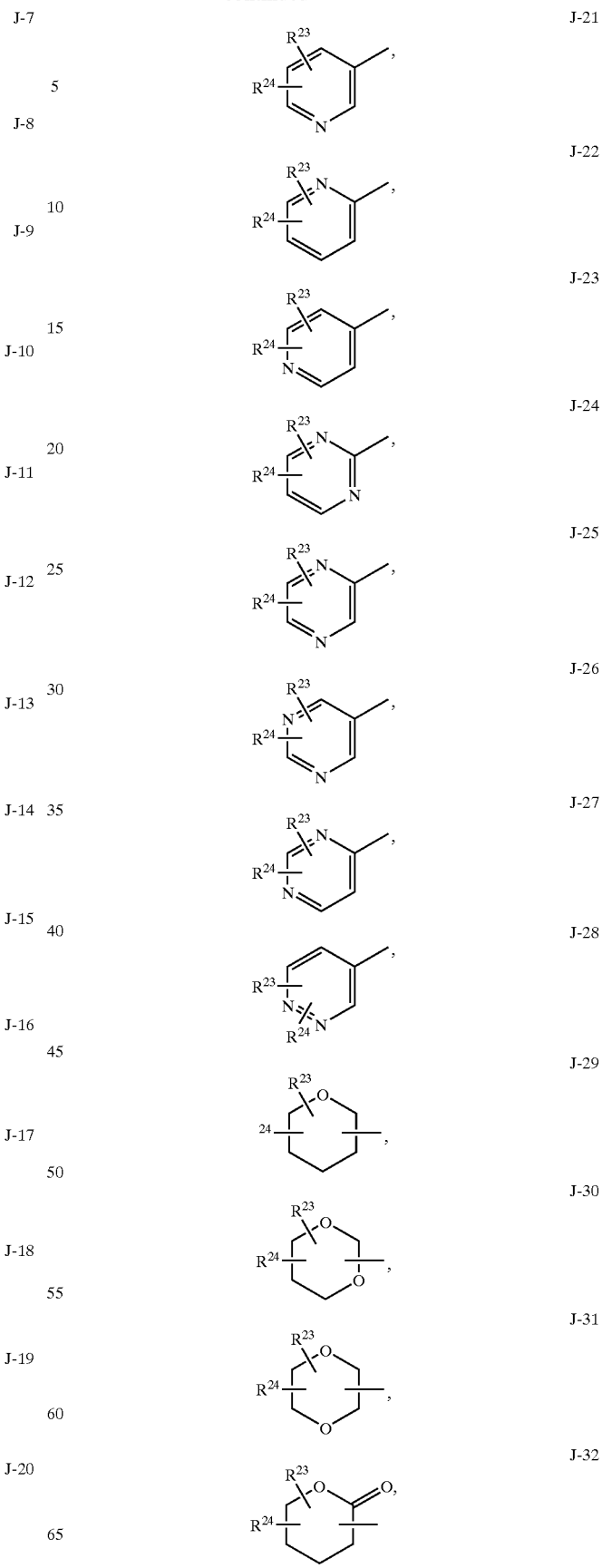

J-33 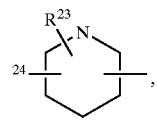

J-34 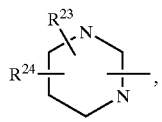

J-35 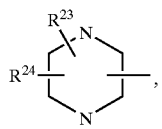

J-36 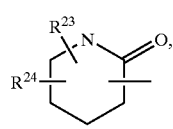

J-37 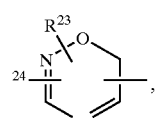

J-38 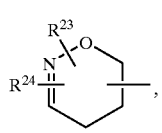

J-39 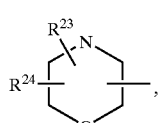

J-40 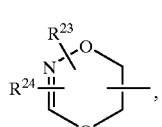

J-41 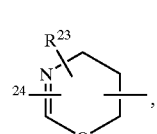

J-42 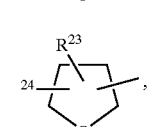

J-43 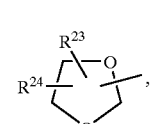

J-44 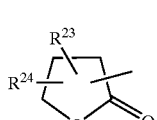

J-45 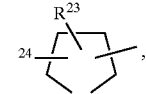

J-46 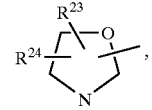

J-47 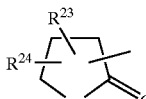

J-48 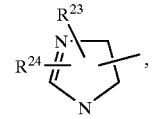

J-49 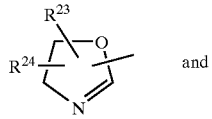 and

J-50 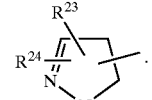

Preferred compounds for reasons of better activity and/or ease of synthesis are:

Preferred 1. Compounds of Formula I above, and agriculturally suitable salts thereof, wherein:

Y is H, $C_1$–$C_6$ alkyl, $C_2$–$C_6$ alkenyl, $C_2$–$C_6$ alkynyl, $C_1$–$C_3$ alkylsulfonyl, $C_3$–$C_6$ cycloalkyl, $C_3$–$C_6$ cycloalkylalkyl, $NR^9R^{10}$, $N\equiv CR^{11}R^{12}$, $OR^7$, $COR^{13}$, $CO_2R^{14}$ or $C_1$–$C_6$ alkyl substituted by at least one group selected from halogen, $C_1$–$C_3$ alkoxy, CN, $NO_2$, $S(O)_rR^{15}$, $COR^{13}$, $CO_2R^{14}$ and phenyl optionally substituted with $R^{23}$ and $R^{24}$;

each $R^1$ and $R^2$ is independently selected from the group consisting of $C_1$–$C_6$ haloalkyl, $C_2$–$C_6$ haloalkenyl, halogen, CN, $NO_2$, $OR^{16}$, $S(O)_rR^{15}$, $OS(O)_2R^{15}$, $CO_2R^{14}$, $C(O)R^{13}$, $C(O)NR^9R^{10}$, $SO_2NR^9R^{10}$, $SF_5$, phenyl optionally substituted with $R^{23}$ and $R^{24}$ and benzyl optionally substituted with $R^{23}$ and $R^{24}$; or when m or n is 2, $(R^1)_2$ can be taken together or $(R^2)_2$ can be talen together as —$OCH_2O$—, —$OCF_2O$—, —$OCH_2CH_2O$—, —$CH_2C(CH_3)_2O$—, —$CF_2CF_2O$ or —$OCF_2CF_2O$—;

$R^3$ is selected from the group consisting of J, $C(R^{17})$=N—O—$R^{18}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxylalkyl, $C_3$–$C_8$ alkoxycarbonylalkyl, $CO_2R^{14}$, $C(O)R^{13}$, $C(O)NR^9R^{10}$, $C(S)NR^9R^{10}$, $C(S)R^{13}$, $C(S)SR^{13}$, CN, and phenyl optionally substituted with $R^{23}$ and $R^{24}$; or $R^3$ is $C_2$–$C_6$ epoxyalkyl optionally substituted with a group selected from $C_1$–$C_3$ alkyl, CN, $C(O)R^{13}$, $CO_2R^{14}$ and phenyl optionally substituted with $R^{23}$ and $R^{24}$; or $R^3$ is $C_1$–$C_6$ alkyl substituted with a group selected from $C(O)NR^9R^{10}$, $COR^{13}$, $CO_2R^{14}$, $S(O)_mR^{15}$, SCN, CN, $C_1$–$C_2$ haloalkoxy, $SiR^{19}R^{20}R^{21}$, NR$^9$R$^{10}$, NO$_2$, OC(O)R$^{13}$, —P(O)(OR$^{22}$)$_2$, phenyl optionally substituted with R$^{23}$ and R$^{24}$, and J;

J is a nonaromatic or aromatic 5- or 6-membered heterocyclic ring, bonded through carbon or nitrogen, containing 1-4 heteroatoms independently selected from the group consisting of 0-2 oxygen, 0-2 sulfur and 0-4 nitrogen, optionally containing one carbonyl moiety and optionally substituted with R$^{23}$ and R$^{24}$;

each R$^7$ is independently H, C$_1$–C$_4$ alkyl, C$_1$–C$_4$ haloalkyl, C$_2$–C$_4$ alkenyl, C$_2$–C$_4$ alkynyl, C$_1$–C$_4$ alkoxy, SO$_2$NR$^9$R$^{10}$, SO$_2$R$^{13}$, COR$^9$, CONR$^9$R$^{10}$, CO$_2$R$^{13}$, phenyl optionally substituted with R$^{23}$ and R$^{24}$ or benzyl optionally substituted with R$^{23}$ and R$^{24}$;

each R$^8$ is independently H, C$_1$–C$_4$ alkyl, C$_1$–C$_4$ alkoxyalkyl, CO$_2$R$^{13}$, SO$_2$R$^{13}$, or benzyl optionally substituted with R$^{23}$ and R$^{24}$;

each R$^9$ and each R$^{11}$ is independently H, C$_1$–C$_4$ alkyl, C$_1$–C$_4$ haloalkyl or phenyl optionally substituted with R$^{23}$ and R$^{24}$;

each R$^{10}$ and each R$^{12}$ is independently H or C$_1$–C$_4$ alkyl; or each pair of R$^9$ and R$^{10}$ when attached to the same atom or each pair of R$^{11}$ and R$^{12}$ when attached to the same atom independently can be taken together as —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$OCH$_2$CH$_2$—, each of which is optionally and independently substituted with 1 or 2 CH$_3$ groups;

each R$^{13}$ and each R$^{15}$ is independently H, C$_1$–C$_4$ alkyl, C$_1$–C$_4$ haloalkyl or phenyl optionally substituted with R$^{23}$ and R$^{24}$;

each R$^{14}$ is independently H, C$_1$–C$_4$ alkyl, C$_1$–C$_4$ haloalkyl or benzyl optionally substituted with R$^{23}$ and R$^{24}$;

R$^{16}$ is H, C$_1$–C$_6$ alkyl, C$_1$–C$_6$ haloalkyl, C$_2$–C$_6$ alkenyl, C$_2$–C$_6$ haloalkenyl, C$_2$–C$_6$ alkynyl, C$_3$–C$_6$ haloalkynyl, C$_2$–C$_6$ alkoxyalkyl, C$_2$–C$_6$ alkylthioalkyl, C$_1$–C$_6$ nitroalkyl, C$_2$–C$_6$ cyanoalkyl, C$_3$–C$_8$ alkoxycarbonylalkyl, C$_3$–C$_6$ cycloalkyl, C$_3$–C$_6$ halocycloalkyl, phenyl optionally substituted with R$^{23}$ and R$^{24}$ and benzyl optionally substituted with R$^{23}$ and R$^{24}$;

R$^{21}$ is selected from the group consisting of H, C$_1$–C$_3$ alkyl and phenyl optionally substituted with R$^{23}$ and R$^{24}$;

each R$^{23}$ is independently selected from the group consisting of 1-2 halogen, CN, NO$_2$, C$_1$–C$_2$ alkyl, C$_1$–C$_2$ haloalkyl, C$_1$–C$_2$ alkoxy, C$_1$–C$_2$ haloalkoxy, C$_1$–C$_2$ alkylthio, C$_1$–C$_2$ haloalkylthio, C$_1$–C$_2$ alkylsulfonyl and C$_1$–C$_2$ haloalkylsulfonyl; and each R$^{24}$ is independently selected from the group consisting of halogen, C$_1$–C$_4$ alkyl, C$_1$–C$_4$ alkoxy, C$_1$–C$_4$ haloalkyl and C$_1$–C$_4$ haloalkoxy.

Most preferred is the compound of Preferred 1:

7-Chloro-9,9α-dihydro-9α-propyl-N-[4-(trifluoromethoxy)phenyl]-1H-indeno[1,2-e]-1,2,4-triazine-3-Carboxamide.

This invention also relates to arthropodicidal compositions comprising arthropodicidally effective amounts of the compounds of the invention and at least one additional component selected from the group consisting of surfactants, solid diluents and liquid diluents. The preferred compositions of the present invention are those which comprise the above preferred compounds.

This invention also relates to a method for controlling arthropods comprising contacting the arthropods or their environment with an arthropodicidally effective amount of the compounds of the invention (e.g., as a composition described herein). The preferred methods of use are those involving the above preferred compounds.

The compounds of Formula I can be prepared by one or more of the following methods and variations as described in Schemes 1–12. The definitions of A, E, G, W, X, Y, R$^2$, R$^3$, Z, R$^4$, R$^5$, R$^6$ and R$^7$ in the compounds of Formulae II–XVI below are as defined above in the Summary of the Invention. Compounds of Formulae Ia–Ic are various subsets of the compounds of Formula I, and all substituents for Formulae Ia–Ic are as defined above for Formula I. In the Schemes, Rk is equivalent to R$^k$ where k is a number from 1 to 7.

Transformations similar to those described in the Schemes have been reported in the references associated with the Schemes. The reactions may be run at temperatures from −100 to 150° C. with temperatures from 0 to 120° C. being preferred. Many solvents are acceptable including ethereal solvents such as diethyl ether, THF, dioxane, or glyme, halocarbon or hydrocarbon solvents such as chlorobenzene, CH$_2$Cl$_2$, hexanes, benzene, toluene or xylene, ketones such as acetone, and polar aprotic solvents such as acetonitrile, dimethylformamide, dimethylacetamide, and dimethylsulfoxide. In some instances aqueous solvents or lower alcohols may be used. One skilled in the art will recognize that the transformations may also be carried out using combinatorial chemistry techniques.

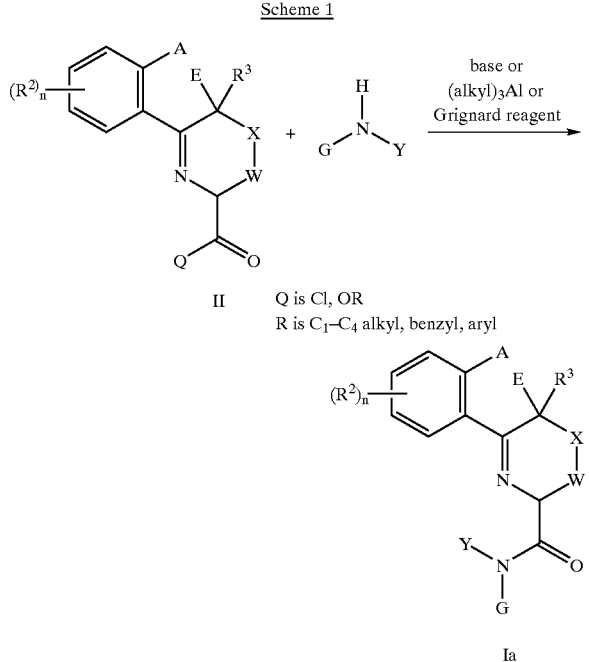

Scheme 1

II    Q is Cl, OR
      R is C$_1$–C$_4$ alkyl, benzyl, aryl

Ia

Compounds of Formula Ia (see Scheme 1 on previous page) can be prepared by reacting a compound of Formula II with a compound of Formula III using procedures known to one skilled in the art (for Q is Cl, see March, *Advanced Organic Chemistry*, 3$^{rd}$ Edition, 1985, p. 370–376; for Q is OR, e.g., *J. Chem. Soc.*, 1954, 1188; *Synth. Commun.*, 1982, 12, 989; *Tetrahedron Lett.*, 1971, 321).

Alternatively, compounds of Formula Ib can be prepared by condensing a compound of Formula IV with a compound of Formula V in the presence of a base.

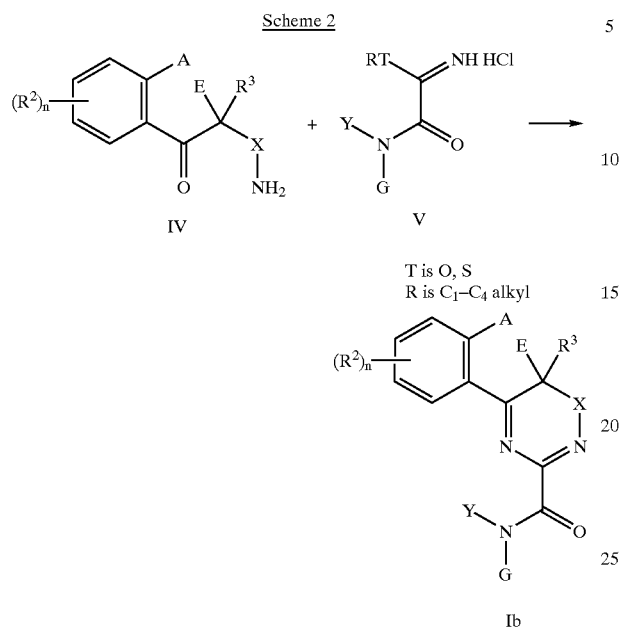

Compounds of Formula IIa can be prepared by reacting a compound of Formula VI with compound of Formula VII using procedures known to one skilled in the art (e.g. *Angew. Chem. int. Ed. Engl.*, 1981, 20, 296).

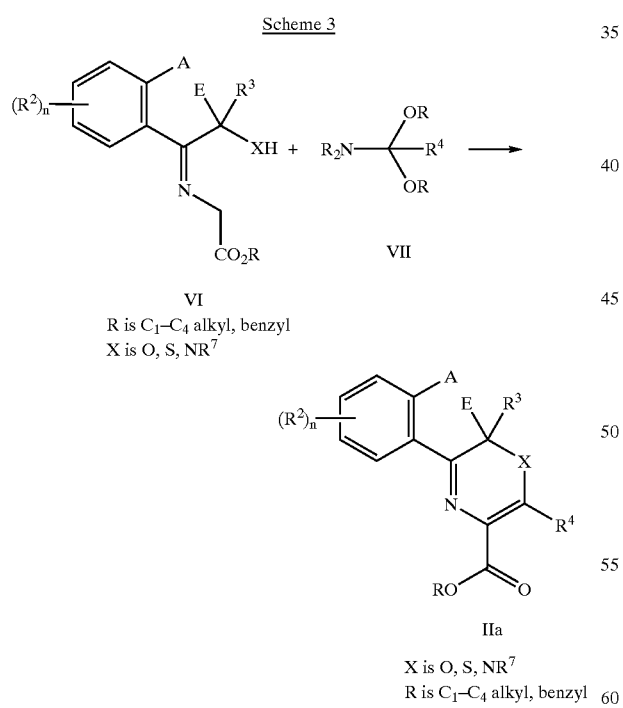

Compounds of Formula IIb (Q is OR) can be prepared by reacting a compound of Formula IV with a compound of Formula VIII using procedures analogous to those described for Scheme 2. One skilled in the art will recognize that compounds of Formula IIb (Q is OR) can be converted into compounds of Formula II wherein Q is Cl using known procedures (e.g. U.S. Pat. No. 5,708,170; March, *Advanced Organic Chemistry*, 3$^{rd}$ Edition, pp. 334–338, 388).

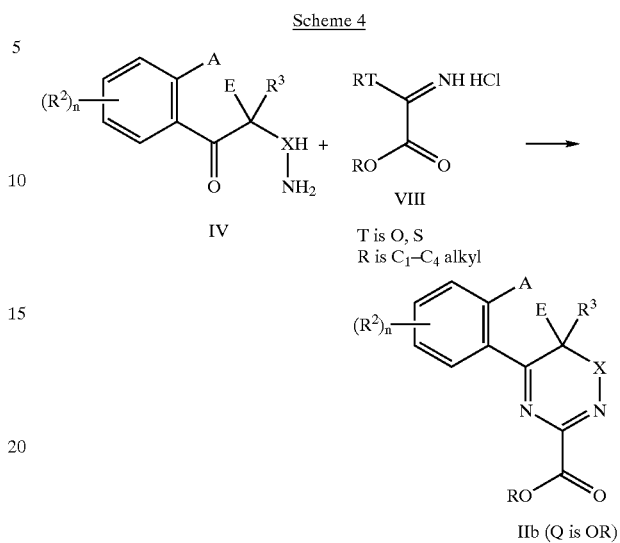

Compounds of Formula X and IVa can be prepared from compounds of Formula IX using procedures that are known to one skilled in the art (e.g., *J. Org. Chem.*, 1988, 53, 2131; *Tetrahedron Lett.*, 1991, 32, 5927; *J. Am. Chem. Soc.*, 1986, 108, 6395).

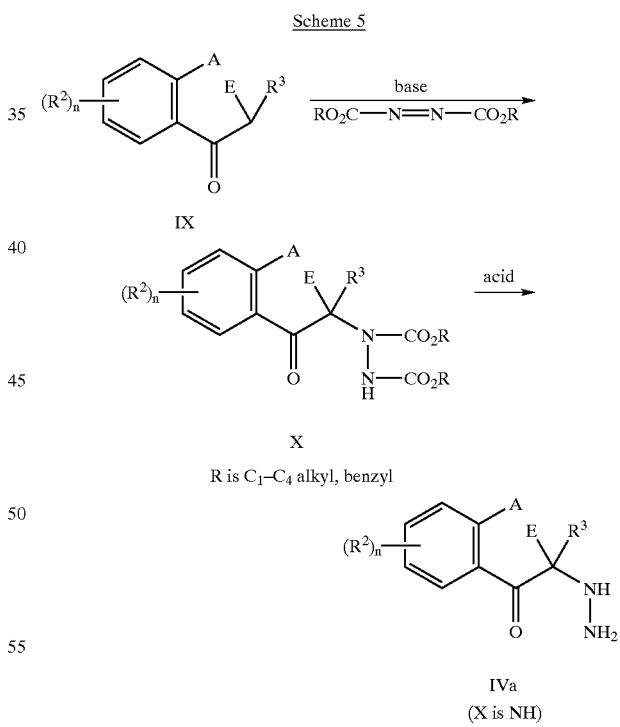

Compounds of Formula IVb (X is O) can be prepared from compounds of Formula XI using procedures that are known to one skilled in the art (e.g., *Chem. Pharm. Bull.*, 1992, 40, 683). Compounds of Formula XI can be prepared from compounds of Formula IX using procedures that are known to one skilled in the art (for LG is Cl, Br, I, e.g., *J. Am. Chem. Soc.*, 1959, 81, 1201; *J. Org. Chem.*, 1968, 33, 419.1; and for LG is OMs ($OSO_2CH_3$), OTf, ($OSO_2CF_3$)

and OTs (OSO$_2$C$_6$H$_4$CH$_3$), e.g., *J. Org. Chem.,* 1985, 50, 5148; *Tetrahedron Lett.,* 1992, 33, 7647; *J. Org. Chem.,* 1982, 47, 2487).

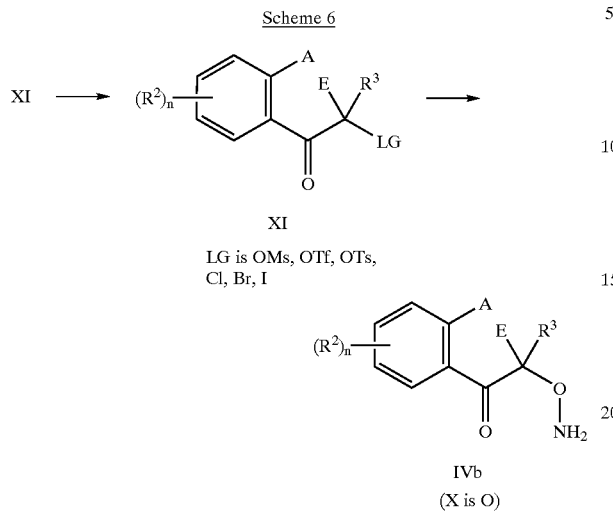

Scheme 6

XI

LG is OMs, OTf, OTs, Cl, Br, I

IVb
(X is O)

Compounds of Formula IVc (X is S) can be prepared by animation of compounds of Formula XII (X is S) using procedures that are known to one skilled in the art (e.g., *J. Org. Chem.,* 1972, 37, 3820; *Synthesis,* 1991, 327; *Synthetic Commun.,* 1986, 16, 899).

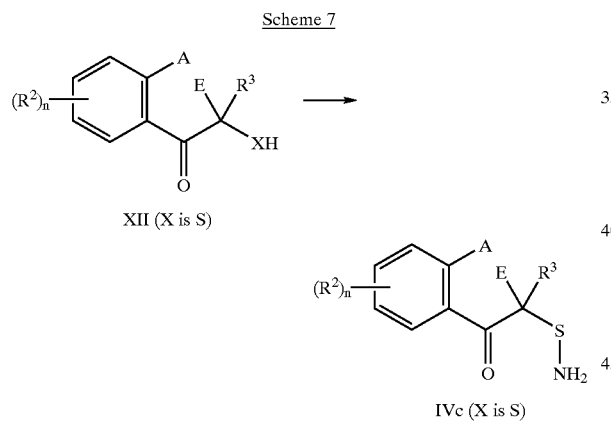

Scheme 7

XII (X is S)

IVc (X is S)

Compounds of Formula IVd (X is CR$^5$R$^6$) can be prepared from compounds of Formula IX using procedures that are known to one skilled in the art (e.g., *J. Am. Chem. Soc.,* 1942, 64, 45; *Chem. Pharm. Bull.,* 1984, 32, 4323).

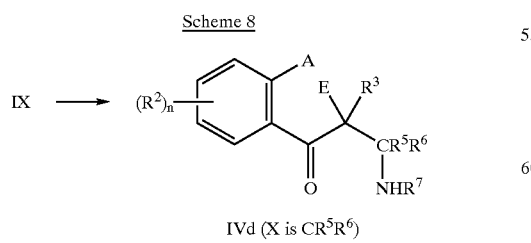

Scheme 8

IVd (X is CR$^5$R$^6$)

Compounds of Formula VI can be prepared by condensation of compounds of Formulae XIIa and XIII using procedures that are known to one skilled in the art (e.g.

March, *Advanced Organic Chemistry,* 3$^{rd}$ Edition, pp. 796–798).

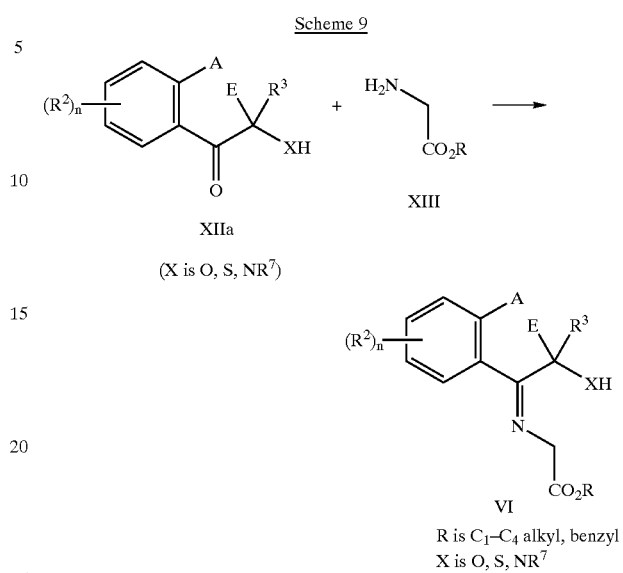

Scheme 9

XIIa
(X is O, S, NR$^7$)

VI
R is C$_1$–C$_4$ alkyl, benzyl
X is O, S, NR$^7$

Compounds of Formula XV can be prepared from compounds of Formula XIV using procedures that are known to one skilled in the art (e.g., *J. Chem. Soc. Chem. Commun.,* 1974, 826; *Justus Liebigs Ann. Chem.,* 1949, 562). Compounds of Formula V can be prepared using procedures described for the reaction in Scheme 10.

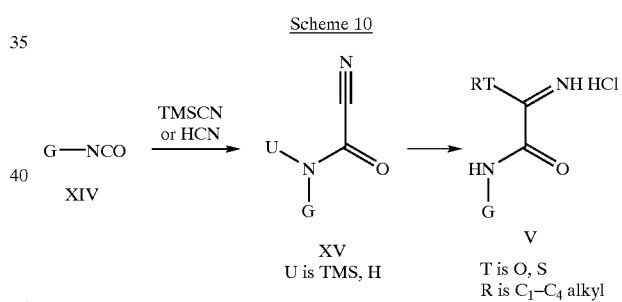

Scheme 10

XIV

XV
U is TMS, H

V
T is O, S
R is C$_1$–C$_4$ alkyl

Compounds of Formula VII can be prepared from compounds of Formula XVI using procedures that are known to one skilled in the art (e.g., *J. Org Chem.,* 1973, 38, 1437; *J. Heterocyclic Chem.,* 1988, 25, 651).

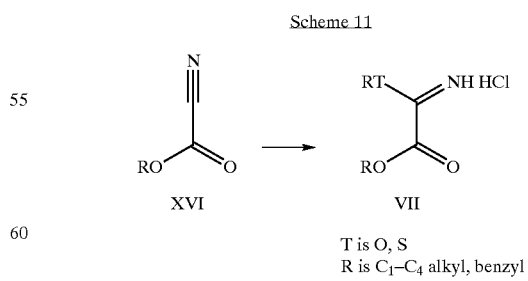

Scheme 11

XVI

VII
T is O, S
R is C$_1$–C$_4$ alkyl, benzyl

Compounds of Formula Ic, compounds of Formula I wherein Z is S, can be prepared by treating compounds of Formula Ia (I wherein Z is O) with thionating reagents such as P$_2$S$_5$ or Lawesson's reagent [2,4-bis(4-methoxyphenyl)-

1,3-dithia-2,4-diphosphetane-2,4-disulfide] as illustrated in Scheme 12 (see *Bull. Soc. Chim. Belg.*, 1978, 87, 229; and *Tetrahedron Lett.*, 1983, 24, 3815).

Scheme 12

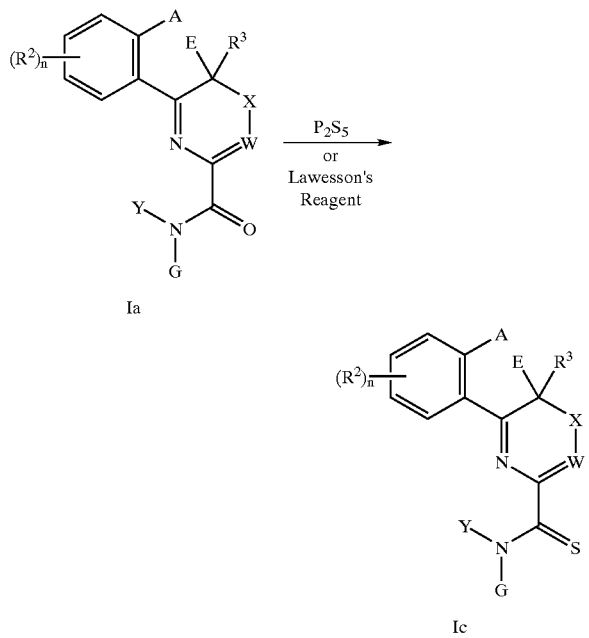

Compounds of Formulae IX and XII can be prepared using procedures described in U.S. Pat. No. 5,708,170.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; $^{19}$F NMR spectra are reported in ppm relative to $CFCl_3$; s is singlet, d is doublet, t is triplet, q is quartet, m is multiplet, dd is doublet of doublets, dt is doublet of triplets, and br s is broad singlet.

EXAMPLE 1

Step A: Preparation of 1-(4-Trifluoromethyl-phenyl)-pentan-1-one

To a suspension of copper bromide-dimethylsulfide complex (11.0 g, 53.5 mmol) in 200 mL ether at −78° C. was added 65 mL of n-BuLi (1.6M, 104.0 mmol) dropwise. The mixture was stirred at −78° C. for 45 min, warmed to −40° C. for 10 min and then re-cooled to −78° C. A solution of 4-trifluoromethylbenzoyl chloride (10.0 g, 48.0 mmol) in 50 mL ether was added dropwise at −78° C. After addition was complete, the reaction was stirred at −78° C. for 30 min, quenched with saturated (sat.) ammonium chloride and allowed to warm to room temperature (RT). The mixture was poured into ether containing ca 10 mL methanol and was washed with a mixture of ammonium chloride/ammonium hydroxide. The combined aqueous layers were extracted with ether. The combined ether layers were dried ($MgSO_4$), filtered and concentrated to give 11.0 g of a solid. $^1$H NMR ($CDCl_3$) δ 8.05 (d,2H), 7.72 (d,2H), 2.99 (t,2H), 1.80–1.67 (m,2H), 1.50–1.35 (m,2H), 0.96 (t,3H). $^{19}$F NMR ($CDCl_3$) δ −63.13.

Step B: Preparation of 1-(4-Trifluoromethyl-phenyl)-2-propyl-propenone

To a solution of the product from Step A (10.6 g, 46.1 mmol) in 80 mL methanol was added 13.8 mL aqueous formaldehyde (37%, 183.5 mmol), piperidine (0.5 mL, 5.0 mmol) and acetic acid (0.5 mL, 8.7 mmol). The mixture was heated under reflux for 62 h, cooled to RT and concentrated in vacuo. The residue was dissolved in ether and dilute aq. NaCl, extracted with ether, dried ($MgSO_4$) and concentrated to give 10.6 g of an oil. $^1$H NMR ($CDCl_3$) δ 7.82 (d,2H0, 7.70 (d,2H), 5.92 (s,1H), 5.61 (s,1H), 2.46 (t,2H), 1.60–1.45 (m,2H), 0.98 (t,3H). $^{19}$F NMR ($CDCl_3$) 67 −63.53.

Step C: Preparation of 2-propyl-5-trifluoromethyl-indan-1-one

The product of Step C (10.5 g, 43.2 mmol) was added dropwise to 50 g of trifluoromethanesulfonic acid cooled to 0° C. The reaction was stirred at 0° C. for 3 h then allowed to warm to RT. After 16 h, the mixture was poured into 250 mL and extracted (3×) with ethyl acetate. The combined organic layers were washed with water (1×), sat. sodium bicarbonate solution (2×), dried ($MgSO_4$), filtered and concentrated. The residue was purifed by chromatography on silica gel eluting with 5% ethyl acetate/hexane to afford 8.8 g of a yellow oil. $^1$H NMR ($CDCl_3$) δ 7.85 (d,1H), 7.73 (s,1H), 7.60 (d,1H), 3.40 (dd,1H), 2.90 (dd,1H), 2.80–2.70 (m,1H), 1.60–1.40 (m,3H), 0.97 (t,3H). $^{19}$F NMR ($CDCl_3$) δ −63.36.

Step D: Preparation of bis(1,1-dimethylethyl) 1-[2.3-dihydro-1-oxo-2-propyl-5-(trifluoromethyl)-1H-inden-2-yl]-1.2-hydrazinedicarboxylic acid To a solution of diisopropylamine (1.3 mL, 9.1 mmol) in 30 mL tetrahydrofuran cooled to −78° C. was added 6.0 mL n-BuLi (1.6M, 9.5 mmol). The mixture was allowed to warm to −20° C. over 20 min, then re-cooled to −78° C. A solution of the product from Step C (2.0 g, 8.3 mmol) in 15 mL tetrahydrofuran was added dropwise. After 30 min, a solution of di-tert-butylazodicarboxylate (2.1 g, 9.1 mmol) in 20 mL tetrahydrofuran was added dropwise. The reaction was allowed to slowly warm to RT and stirred overnight. Water was added and the mixture was extracted with ethyl acetate, dried ($MgSO_4$), filtered and concentrated. The residue was purified by chromatography on silica gel eluting with 10% ethyl acetate/hexane to afford 2.92 g of a white solid, m.p. 135–137° C.

Step E: Preparation of methyl 9.9α-dihydro-9α-propyl-7-(trifluoromethyl)-1H-indeno[1,2-e]-1,2,4-triazine-3-Carboxylate To a solution of the product from Step D (1.5 g, 3.2 mmol) in 5 mL dichloromethane and 1 mL toluene was added 2 mL trifluoroacetic acid. After 4 h, the solvent was removed in vacuo. The residue was suspended in hexane and the solvent was removed (2×). A solution of the residue dissolved in 20 mL methanol was treated with ethyl carbomethoxyformimidate hydrochloride (0.6 g, 3.5 mmol), prepared according to the procedure in *J. Heterocyclic Chem.* 1988, 25, 651. After 24 h, solid sodium bicarbonate (ca. 1 g) was added. The mixture was poured into water, extracted with ethyl acetate, dried ($MgSO_4$), filtered and concentrated. The solids were triturated with hexanes and dried in vacuo to provide 0.5 g of a yellow solid, m.p. 141–142° C.

Step F: Preparation of 9,9α-dihydro-9α-propyl-N-[4-(trifluoromethoxy)phenyl]-7-(trifluoromethyl)-1H-indeno[1,2-e]-1,2,4-triazine-3-carboxamide To a solution of 4-trifluoromethoxyaniline (0.68 g, 3.9 mmol) dissolved in 10 mL tetrahydrofuran was added 1.3 mL of methylmagnesium chloride (3.0M in tetrahydrofuran, 3.9 mmol). After 10 min, the mixture was added to a solution of the product from Step E (0.20 g, 0.59 mmol) in 7 mL tetrahydrofuran in one portion. After 16 h, ether and 1N HCl was added. The organic layer was washed with 1N HCl (2×), sat. sodium bicarbonate solution (1×), dried ($MgSO_4$), filtered and concentrated. The residue was taken up in ether. Solids formed on sitting. The solids were washed with ether and hexane and dried in vacuo to afford 0.11 g of a solid, m.p. 192–194° C. A second crop of 0.18 g of product was also isolated.

EXAMPLE 2

Preparation of N-(4-bromophenyl)-9,9α-dihydro-9α-propyl-7-(trifluoromethyl)-1H-indeno[1,2,-e]-1.2,4-triazine-3-carboxamide To a solution of 4-bromoaniline (0.67 g, 3.9 mmol) dissolved in 10 mL tetrahydrofuran was added 1.3 mL of methylmagnesium chloride (3.0M in tetrahydrofuran, 3.9 mmol). After 10 min, the mixture was added to a solution of the product from Ex. 1, Step E (0.2 g, 0.59 mmol) in 7 mL tetrahydrofuran in one portion. After 16 h, ether and 1N HCl was added. The organic layer was washed with 1N HCl (2×), sat. sodium bicarbonate solution (1×), dried ($MgSO_4$), filtered and concentrated. The residue was taken up in ether. Solids formed on sitting. The solids were washed with ether and hexane and dried in vacuo to afford 0.16 g of a solid, m.p. 198–199° C.

By the procedures described herein together with methods known in the art, the following compounds of Tables 1 to 3 can be prepared. The following abbreviations are used in the Tables: t is tertiary, s is secondary, n is normal, i is iso, c is cyclo, Me is methyl, Et is ethyl, Pr is propyl, i-Pr is isopropyl, Bu is butyl, Ph is phenyl, OMe is methoxy, OEt is ethoxy and CN is cyano.

TABLE 1

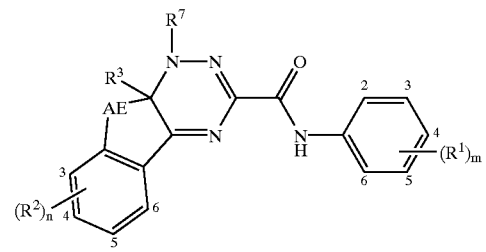

when AE is listed as H, H, there is no link between the rings at AE

| AE | $(R^1)_m$ | $(R^2)_n$ | $R^3$ | $R^7$ |
|---|---|---|---|---|
| $CH_2$ | 4-$OCF_3$ | 4-Cl | Me | H |
| $CH_2$ | 4-$OCF_3$ | 4-Cl | Et | H |
| $CH_2$ | 4-$OCF_3$ | 4-Cl | n-Pr | H |
| $CH_2$ | 4-$OCF_3$ | 4-Cl | i-Pr | H |
| $CH_2$ | 4-$OCF_3$ | 4-Cl | n-Bu | H |
| $CH_2$ | 4-$OCF_3$ | 4-Cl | i-Bu | H |
| $CH_2$ | 4-$OCF_3$ | 4-Cl | c-Pr | H |
| $CH_2$ | 4-$OCF_3$ | 4-Cl | Ph | H |
| $CH_2$ | 4-$OCF_3$ | 4-Cl | 4-Cl—Ph | H |
| $CH_2$ | 4-$OCF_3$ | 4-Cl | 4-F—Ph | H |
| $CH_2$ | 4-$OCF_3$ | 4-Cl | 4-CN—Ph | H |
| $CH_2$ | 4-$OCF_3$ | 4-Cl | $CO_2Me$ | H |
| $CH_2$ | 4-$CF_3$ | 4-Cl | Me | H |
| $CH_2$ | 4-$CF_3$ | 4-Cl | Et | H |
| $CH_2$ | 4-$CF_3$ | 4-Cl | n-Pr | H |
| $CH_2$ | 4-$CF_3$ | 4-Cl | i-Pr | H |
| $CH_2$ | 4-$CF_3$ | 4-Cl | n-Bu | H |
| $CH_2$ | 4-$CF_3$ | 4-Cl | i-Bu | H |
| $CH_2$ | 4-$CF_3$ | 4-Cl | c-Pr | H |
| $CH_2$ | 4-$CF_3$ | 4-Cl | Ph | H |
| $CH_2$ | 4-$CF_3$ | 4-Cl | 4-Cl—Ph | H |
| $CH_2$ | 4-$CF_3$ | 4-Cl | 4-F—Ph | H |
| $CH_2$ | 4-$CF_3$ | 4-Cl | 4-CN—Ph | H |
| $CH_2$ | 4-$CF_3$ | 4-Cl | $CO_2Me$ | H |
| $CH_2$ | 4-$OCF_3$ | 4-$CF_3$ | Me | H |
| $CH_2$ | 4-$OCF_3$ | 4-$CF_3$ | Et | H |
| $CH_2$ | 4-$OCF_3$ | 4-$CF_3$ | n-Pr | H |
| $CH_2$ | 4-$OCF_3$ | 4-$CF_3$ | i-Pr | H |
| $CH_2$ | 4-$OCF_3$ | 4-$CF_3$ | n-Bu | H |
| $CH_2$ | 4-$OCF_3$ | 4-$CF_3$ | i-Bu | H |
| $CH_2$ | 4-$OCF_3$ | 4-$CF_3$ | c-Pr | H |
| $CH_2$ | 4-$OCF_3$ | 4-$CF_3$ | Ph | H |
| $CH_2$ | 4-$OCF_3$ | 4-$CF_3$ | 4-Cl—Ph | H |
| $CH_2$ | 4-$OCF_3$ | 4-$CF_3$ | 4-F—Ph | H |
| $CH_2$ | 4-$OCF_3$ | 4-$CF_3$ | 4-CN—Ph | H |
| $CH_2$ | 4-$OCF_3$ | 4-$CF_3$ | $CO_2Me$ | H |
| $CH_2$ | 4-$CF_3$ | 4-$CF_3$ | Me | H |
| $CH_2$ | 4-$CF_3$ | 4-$CF_3$ | Et | H |
| $CH_2$ | 4-$CF_3$ | 4-$CF_3$ | n-Pr | H |
| $CH_2$ | 4-$CF_3$ | 4-$CF_3$ | i-Pr | H |
| $CH_2$ | 4-$CF_3$ | 4-$CF_3$ | n-Bu | H |
| $CH_2$ | 4-$CF_3$ | 4-$CF_3$ | i-Bu | H |
| $CH_2$ | 4-$CF_3$ | 4-$CF_3$ | c-Pr | H |
| $CH_2$ | 4-$CF_3$ | 4-$CF_3$ | Ph | H |
| $CH_2$ | 4-$CF_3$ | 4-$CF_3$ | 4-Cl—Ph | H |
| $CH_2$ | 4-$CF_3$ | 4-$CF_3$ | 4-F—Ph | H |
| $CH_2$ | 4-$CF_3$ | 4-$CF_3$ | 4-CN—Ph | H |
| $CH_2$ | 4-$CF_3$ | 4-$CF_3$ | $CO_2Me$ | H |
| $CH_2$ | 4-$OCF_3$ | 4-F | Me | H |
| $CH_2$ | 4-$OCF_3$ | 4-F | Et | H |
| $CH_2$ | 4-$OCF_3$ | 4-F | n-Pr | H |
| $CH_2$ | 4-$OCF_3$ | 4-F | i-Pr | H |
| $CH_2$ | 4-$OCF_3$ | 4-F | n-Bu | H |
| $CH_2$ | 4-$OCF_3$ | 4-F | i-Bu | H |
| $CH_2$ | 4-$OCF_3$ | 4-F | c-Pr | H |
| $CH_2$ | 4-$OCF_3$ | 4-F | Ph | H |
| $CH_2$ | 4-$OCF_3$ | 4-F | 4-Cl—Ph | H |
| $CH_2$ | 4-$OCF_3$ | 4-F | 4-F—Ph | H |
| $CH_2$ | 4-$OCF_3$ | 4-F | 4-CN—Ph | H |
| $CH_2$ | 4-$OCF_3$ | 4-F | $CO_2Me$ | H |
| $CH_2$ | 4-$OCF_3$ | 3-F | Me | H |
| $CH_2$ | 4-$OCF_3$ | 3-F | Et | H |
| $CH_2$ | 4-$OCF_3$ | 3-F | n-Pr | H |

TABLE 1-continued

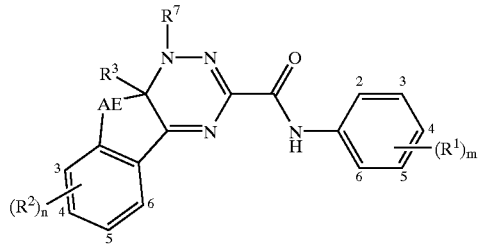

when AE is listed as H, H, there is no link between the rings at AE

| AE | (R¹)ₘ | (R²)ₙ | R³ | R⁷ |
|---|---|---|---|---|
| CH₂ | 4-OCF₃ | 3-F | i-Pr | H |
| CH₂ | 4-OCF₃ | 3-F | n-Bu | H |
| CH₂ | 4-OCF₃ | 3-F | i-Bu | H |
| CH₂ | 4-OCF₃ | 3-F | c-Pr | H |
| CH₂ | 4-OCF₃ | 3-F | Ph | H |
| CH₂ | 4-OCF₃ | 3-F | 4-Cl—Ph | H |
| CH₂ | 4-OCF₃ | 3-F | 4-F—Ph | H |
| CH₂ | 4-OCF₃ | 3-F | 4-CN—Ph | H |
| CH₂ | 4-OCF₃ | 3-F | CO₂Me | H |
| CH₂ | 4-OCF₃ | 3-Cl | Me | H |
| CH₂ | 4-OCF₃ | 3-Cl | Et | H |
| CH₂ | 4-OCF₃ | 3-Cl | n-Pr | H |
| CH₂ | 4-OCF₃ | 3-Cl | i-Pr | H |
| CH₂ | 4-OCF₃ | 3-Cl | n-Bu | H |
| CH₂ | 4-OCF₃ | 3-Cl | i-Bu | H |
| CH₂ | 4-OCF₃ | 3-Cl | c-Pr | H |
| CH₂ | 4-OCF₃ | 3-Cl | Ph | H |
| CH₂ | 4-OCF₃ | 3-Cl | 4-Cl—Ph | H |
| CH₂ | 4-OCF₃ | 3-Cl | 4-F—Ph | H |
| CH₂ | 4-OCF₃ | 3-Cl | 4-CN—Ph | H |
| CH₂ | 4-OCF₃ | 3-Cl | CO₂Me | H |
| CH₂ | 4-OCF₃ | 4-Br | Me | H |
| CH₂ | 4-OCF₃ | 4-Br | Et | H |
| CH₂ | 4-OCF₃ | 4-Br | n-Pr | H |
| CH₂ | 4-OCF₃ | 4-Br | i-Pr | H |
| CH₂ | 4-OCF₃ | 4-Br | n-Bu | H |
| CH₂ | 4-OCF₃ | 4-Br | i-Bu | H |
| CH₂ | 4-OCF₃ | 4-Br | c-Pr | H |
| CH₂ | 4-OCF₃ | 4-Br | Ph | H |
| CH₂ | 4-OCF₃ | 4-Br | 4-Cl—Ph | H |
| CH₂ | 4-OCF₃ | 4-Br | 4-F—Ph | H |
| CH₂ | 4-OCF₃ | 4-Br | 4-CN—Ph | H |
| CH₂ | 4-OCF₃ | 4-Br | CO₂Me | H |
| O | 4-OCF₃ | 4-Cl | Me | H |
| O | 4-OCF₃ | 4-Cl | Et | H |
| O | 4-OCF₃ | 4-Cl | n-Pr | H |
| O | 4-OCF₃ | 4-Cl | i-Pr | H |
| O | 4-OCF₃ | 4-Cl | n-Bu | H |
| O | 4-OCF₃ | 4-Cl | i-Bu | H |
| O | 4-OCF₃ | 4-Cl | c-Pr | H |
| O | 4-OCF₃ | 4-Cl | Ph | H |
| O | 4-OCF₃ | 4-Cl | 4-Cl—Ph | H |
| O | 4-OCF₃ | 4-Cl | 4-F—Ph | H |
| O | 4-OCF₃ | 4-Cl | 4-CN—Ph | H |
| O | 4-OCF₃ | 4-Cl | CO₂Me | H |
| O | 4-CF₃ | 4-Cl | Me | H |
| O | 4-CF₃ | 4-Cl | Et | H |
| O | 4-CF₃ | 4-Cl | n-Pr | H |
| O | 4-CF₃ | 4-Cl | i-Pr | H |
| O | 4-CF₃ | 4-Cl | n-Bu | H |
| O | 4-CF₃ | 4-Cl | i-Bu | H |
| O | 4-CF₃ | 4-Cl | c-Pr | H |
| O | 4-CF₃ | 4-Cl | Ph | H |
| O | 4-CF₃ | 4-Cl | 4-Cl—Ph | H |
| O | 4-CF₃ | 4-Cl | 4-F—Ph | H |
| O | 4-CF₃ | 4-Cl | 4-CN—Ph | H |
| O | 4-CF₃ | 4-Cl | CO₂Me | H |
| O | 4-OCF₃ | 4-CF₃ | Me | H |
| O | 4-OCF₃ | 4-CF₃ | Et | H |
| O | 4-OCF₃ | 4-CF₃ | n-Pr | H |
| O | 4-OCF₃ | 4-CF₃ | i-Pr | H |
| O | 4-OCF₃ | 4-CF₃ | n-Bu | H |
| O | 4-OCF₃ | 4-CF₃ | i-Bu | H |

TABLE 1-continued

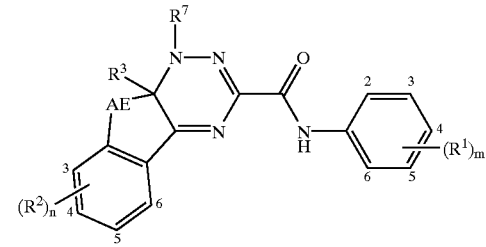

when AE is listed as H, H, there is no link between the rings at AE

| AE | (R¹)ₘ | (R²)ₙ | R³ | R⁷ |
|---|---|---|---|---|
| O | 4-OCF₃ | 4-CF₃ | c-Pr | H |
| O | 4-OCF₃ | 4-CF₃ | Ph | H |
| O | 4-OCF₃ | 4-CF₃ | 4-Cl—Ph | H |
| O | 4-OCF₃ | 4-CF₃ | 4-F—Ph | H |
| O | 4-OCF₃ | 4-CF₃ | 4-CN—Ph | H |
| O | 4-OCF₃ | 4-CF₃ | CO₂Me | H |
| O | 4-CF₃ | 4-CF₃ | Me | H |
| O | 4-CF₃ | 4-CF₃ | Et | H |
| O | 4-CF₃ | 4-CF₃ | n-Pr | H |
| O | 4-CF₃ | 4-CF₃ | i-Pr | H |
| O | 4-CF₃ | 4-CF₃ | n-Bu | H |
| O | 4-CF₃ | 4-CF₃ | i-Bu | H |
| O | 4-CF₃ | 4-CF₃ | c-Pr | H |
| O | 4-CF₃ | 4-CF₃ | Ph | H |
| O | 4-CF₃ | 4-CF₃ | 4-Cl—Ph | H |
| O | 4-CF₃ | 4-CF₃ | 4-F—Ph | H |
| O | 4-CF₃ | 4-CF₃ | 4-CN—Ph | H |
| O | 4-CF₃ | 4-CF₃ | CO₂Me | H |
| CH₂ | 4-OCF₃ | 4-CF₃ | Me | H |
| CH₂ | 4-OCF₃ | 4-CF₃ | Et | H |
| H, H | 4-OCF₃ | 5-CF₃ | n-Pr | H |
| H, H | 4-OCF₃ | 5-CF₃ | i-Pr | H |
| H, H | 4-OCF₃ | 5-CF₃ | n-Bu | H |
| H, H | 4-OCF₃ | 5-CF₃ | i-Bu | H |
| H, H | 4-OCF₃ | 5-CF₃ | c-Pr | H |
| H, H | 4-OCF₃ | 5-CF₃ | Ph | H |
| H, H | 4-OCF₃ | 5-CF₃ | 4-Cl—Ph | H |
| H, H | 4-OCF₃ | 5-CF₃ | 4-F—Ph | H |
| H, H | 4-OCF₃ | 5-CF₃ | 4-CN—Ph | H |
| H, H | 4-OCF₃ | 5-CF₃ | CO₂Me | H |
| H, H | 4-CF₃ | 5-CF₃ | Me | H |
| H, H | 4-CF₃ | 5-CF₃ | Et | H |
| H, H | 4-CF₃ | 5-CF₃ | n-Pr | H |
| H, H | 4-CF₃ | 5-CF₃ | i-Pr | H |
| H, H | 4-CF₃ | 5-CF₃ | n-Bu | H |
| H, H | 4-CF₃ | 5-CF₃ | i-Bu | H |
| H, H | 4-CF₃ | 5-CF₃ | c-Pr | H |
| H, H | 4-CF₃ | 5-CF₃ | Ph | H |
| H, H | 4-CF₃ | 5-CF₃ | 4-Cl—Ph | H |
| H, H | 4-CF₃ | 5-CF₃ | 4-F—Ph | H |
| H, H | 4-CF₃ | 5-CF₃ | 4-CN—Ph | H |
| H, H | 4-CF₃ | 5-CF₃ | CO₂Me | H |
| CH₂ | 4-OCF₃ | 4-CF₃ | n-Pr | Me |
| CF₂ | 4-OCF₃ | 4-CF₃ | n-Pr | Et |
| CF₂ | 4-OCF₃ | 4-CF₃ | n-Pr | Allyl |
| CH₂ | 4-OCF₃ | 4-CF₃ | n-Pr | Propargyl |
| CH₂ | 4-OCF₃ | 4-CF₃ | n-Pr | Acetyl |
| CH₂ | 4-OCF₃ | 4-CF₃ | n-Pr | Propionyl |
| CH₂ | 4-OCF₃ | 4-CF₃ | n-Pr | Butyryl |
| CH₂ | 4-OCF₃ | 4-CF₃ | n-Pr | Benzoyl |
| CH₂ | 4-OCF₃ | 4-CF₃ | n-Pr | CO₂Me |
| CH₂ | 4-OCF₃ | 4-CF₃ | n-Pr | CO₂Et |
| CH₂ | 4-OCF₃ | 4-CF₃ | n-Pr | COCO₂Me |
| CH₂ | 4-OCF₃ | 4-CF₃ | n-Pr | COCO₂Et |
| CH₂ | 4-OCF₃ | 4-CF₃ | n-Pr | Benzyl |
| CH₂ | 4-OCF₃ | 4-CF₃ | n-Pr | CO₂Ph |
| CH₂ | 4-OCF₃ | 4-CF₃ | n-Pr | CO-c-Pr |
| CH₂ | 4-OCF₃ | 4-CF₃ | n-Pr | CO-i-Pr |
| CH₂ | 4-OCF₃ | 4-CF₃ | n-Pr | CONMe₂ |
| CH₂ | 4-OCF₃ | 4-CF₃ | n-Pr | CONHMe |
| CH₂ | 4-OCF₃ | 4-Cl | n-Pr | Me |
| CH₂ | 4-OCF₃ | 4-Cl | n-Pr | Et |
| CH₂ | 4-OCF₃ | 4-Cl | n-Pr | Allyl |

TABLE 1-continued

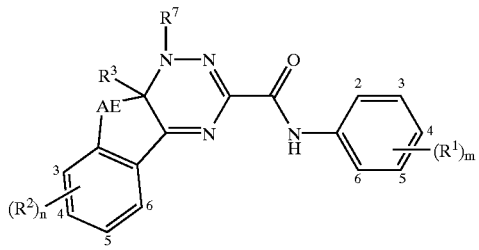

when AE is listed as H, H, there is no link between the rings at AE

| AE | $(R^1)_m$ | $(R^2)_n$ | $R^3$ | $R^7$ |
|---|---|---|---|---|
| $CH_2$ | 4-$OCF_3$ | 4-Cl | n-Pr | Propargyl |
| $CH_2$ | 4-$OCF_3$ | 4-Cl | n-Pr | Acetyl |
| $CH_2$ | 4-$OCF_3$ | 4-Cl | n-Pr | Propionyl |
| $CH_2$ | 4-$OCF_3$ | 4-Cl | n-Pr | Butyryl |
| $CH_2$ | 4-$OCF_3$ | 4-Cl | n-Pr | Benzoyl |
| $CH_2$ | 4-$OCF_3$ | 4-Cl | n-Pr | $CO_2Me$ |
| $CH_2$ | 4-$OCF_3$ | 4-Cl | n-Pr | $CO_2Et$ |
| $CH_2$ | 4-$OCF_3$ | 4-Cl | n-Pr | $COCO_2Me$ |
| $CH_2$ | 4-$OCF_3$ | 4-Cl | n-Pr | $COCO_2Et$ |
| $CH_2$ | 4-$OCF_3$ | 4-Cl | n-Pr | Benzyl |
| $CH_2$ | 4-$OCF_3$ | 4-Cl | n-Pr | $CO_2Ph$ |
| $CH_2$ | 4-$OCF_3$ | 4-Cl | n-Pr | CO-c-Pr |
| $CH_2$ | 4-$OCF_3$ | 4-Cl | n-Pr | CO-i-Pr |
| $CH_2$ | 4-$OCF_3$ | 4-Cl | n-Pr | $CONMe_2$ |
| $CH_2$ | 4-$OCF_3$ | 4-Cl | n-Pr | CONHMe |
| $CH_2$ | 4-Br | 4-Cl | Me | H |
| $CH_2$ | 4-Br | 4-Cl | Et | H |
| $CH_2$ | 4-Br | 4-Cl | n-Pr | H |
| $CH_2$ | 4-Br | 4-Cl | i-Pr | H |
| $CH_2$ | 4-Br | 4-Cl | n-Bu | H |
| $CH_2$ | 4-Br | 4-Cl | i-Bu | H |
| $CH_2$ | 4-Br | 4-Cl | c-Pr | H |
| $CH_2$ | 4-Br | 4-Cl | Ph | H |
| $CH_2$ | 4-Br | 4-Cl | 4-Cl—Ph | H |
| $CH_2$ | 4-Br | 4-Cl | 4-F—Ph | H |
| $CH_2$ | 4-Br | 4-Cl | 4-CN—Ph | H |
| $CH_2$ | 4-Br | 4-Cl | $CO_2Me$ | H |
| $OCH_2$ | 4-$OCF_3$ | 3-Cl | n-Pr | H |
| $CH_2O$ | 4-$OCF_3$ | 3-Cl | n-Pr | H |
| S | 4-$OCF_3$ | 4-Cl | n-Pr | H |
| NH | 4-$OCF_3$ | 4-Cl | n-Pr | H |
| $CH_2CH_2$ | 4-$OCF_3$ | 3-Cl | n-Pr | H |
| $NHCH_2$ | 4-$OCF_3$ | 3-Cl | n-Pr | H |
| $CH_2NH$ | 4-$OCF_3$ | 3-Cl | n-Pr | H |

TABLE 2

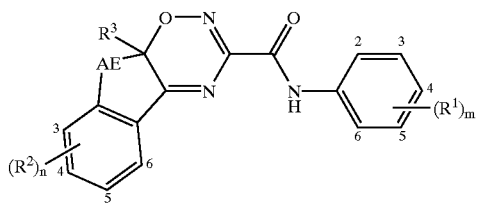

when AE is listed as H, H, there is no link between the rings at AE

| AE | $(R^1)_m$ | $(R^2)_n$ | $R^3$ |
|---|---|---|---|
| $CH_2$ | 4-$OCF_3$ | 4-Cl | Me |
| $CH_2$ | 4-$OCF_3$ | 4-Cl | Et |
| $CH_2$ | 4-$OCF_3$ | 4-Cl | n-Pr |
| $CH_2$ | 4-$OCF_3$ | 4-Cl | i-Pr |
| $CH_2$ | 4-$OCF_3$ | 4-Cl | n-Bu |
| $CH_2$ | 4-$OCF_3$ | 4-Cl | i-Bu |
| $CH_2$ | 4-$OCF_3$ | 4-Cl | c-Pr |
| $CH_2$ | 4-$OCF_3$ | 4-Cl | Ph |
| $CH_2$ | 4-$OCF_3$ | 4-Cl | 4-Cl—Ph |
| $CH_2$ | 4-$OCF_3$ | 4-Cl | 4-F—Ph |

TABLE 2-continued

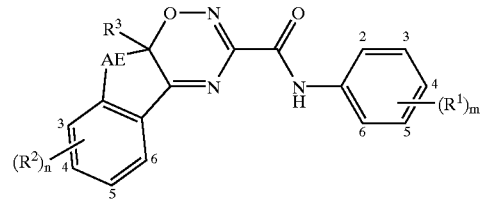

when AE is listed as H, H, there is no link between the rings at AE

| AE | $(R^1)_m$ | $(R^2)_n$ | $R^3$ |
|---|---|---|---|
| $CH_2$ | 4-$OCF_3$ | 4-Cl | 4-CN—Ph |
| $CH_2$ | 4-$OCF_3$ | 4-Cl | $CO_2Me$ |
| $CH_2$ | 4-$CF_3$ | 4-Cl | Me |
| $CH_2$ | 4-$CF_3$ | 4-Cl | Et |
| $CH_2$ | 4-$CF_3$ | 4-Cl | n-Pr |
| $CH_2$ | 4-$CF_3$ | 4-Cl | i-Pr |
| $CH_2$ | 4-$CF_3$ | 4-Cl | n-Bu |
| $CH_2$ | 4-$CF_3$ | 4-Cl | i-Bu |
| $CH_2$ | 4-$CF_3$ | 4-Cl | c-Pr |
| $CH_2$ | 4-$CF_3$ | 4-Cl | Ph |
| $CH_2$ | 4-$CF_3$ | 4-Cl | 4-Cl—Ph |
| $CH_2$ | 4-$CF_3$ | 4-Cl | 4-F—Ph |
| $CH_2$ | 4-$CF_3$ | 4-Cl | 4-CN—Ph |
| $CH_2$ | 4-$CF_3$ | 4-Cl | $CO_2Me$ |
| $CH_2$ | 4-$OCF_3$ | 4-$CF_3$ | Me |
| $CH_2$ | 4-$OCF_3$ | 4-$CF_3$ | Et |
| $CH_2$ | 4-$OCF_3$ | 4-$CF_3$ | n-Pr |
| $CH_2$ | 4-$OCF_3$ | 4-$CF_3$ | i-Pr |
| $CH_2$ | 4-$OCF_3$ | 4-$CF_3$ | n-Bu |
| $CH_2$ | 4-$OCF_3$ | 4-$CF_3$ | i-Bu |
| $CH_2$ | 4-$OCF_3$ | 4-$CF_3$ | c-Pr |
| $CH_2$ | 4-$OCF_3$ | 4-$CF_3$ | Ph |
| $CH_2$ | 4-$OCF_3$ | 4-$CF_3$ | 4-Cl—Ph |
| $CH_2$ | 4-$OCF_3$ | 4-$CF_3$ | 4-F—Ph |
| $CH_2$ | 4-$CCF_3$ | 4-$CF_3$ | 4-CN—Ph |
| $CH_2$ | 4-$OCF_3$ | 4-$CF_3$ | $CO_2Me$ |
| $CH_2$ | 4-$CF_3$ | 4-$CF_3$ | Me |
| $CH_2$ | 4-$CF_3$ | 4-$CF_3$ | Et |
| $CH_2$ | 4-$CF_3$ | 4-$CF_3$ | n-Pr |
| $CH_2$ | 4-$CF_3$ | 4-$CF_3$ | i-Pr |
| $CH_2$ | 4-$CF_3$ | 4-$CF_3$ | n-Bu |
| $CH_2$ | 4-$CF_3$ | 4-$CF_3$ | i-Bu |
| $CH_2$ | 4-$CF_3$ | 4-$CF_3$ | c-Pr |
| $CH_2$ | 4-$CF_3$ | 4-$CF_3$ | Ph |
| $CH_2$ | 4-$CF_3$ | 4-$CF_3$ | 4-Cl—Ph |
| $CH_2$ | 4-$CF_3$ | 4-$CF_3$ | 4-F—Ph |
| $CH_2$ | 4-$CF_3$ | 4-$CF_3$ | 4-CN—Ph |
| $CH_2$ | 4-$CF_3$ | 4-$CF_3$ | $CO_2Me$ |
| $CH_2$ | 4-$OCF_3$ | 4-F | Me |
| $CH_2$ | 4-$OCF_3$ | 4-F | Et |
| $CH_2$ | 4-$OCF_3$ | 4-F | n-Pr |
| $CH_2$ | 4-$OCF_3$ | 4-F | i-Pr |
| $CH_2$ | 4-$OCF_3$ | 4-F | n-Bu |
| $CH_2$ | 4-$OCF_3$ | 4-F | i-Bu |
| $CH_2$ | 4-$OCF_3$ | 4-F | c-Pr |
| $CH_2$ | 4-$OCF_3$ | 4-F | Ph |
| $CH_2$ | 4-$OCF_3$ | 4-F | 4-Cl—Ph |
| $CH_2$ | 4-$OCF_3$ | 4-F | 4-F—Ph |
| $CH_2$ | 4-$OCF_3$ | 4-F | 4-CN—Ph |
| $CH_2$ | 4-$OCF_3$ | 4-F | $CO_2Me$ |
| $CH_2$ | 4-$OCF_3$ | 3-F | Me |
| $CH_2$ | 4-$OCF_3$ | 3-F | Et |
| $CH_2$ | 4-$OCF_3$ | 3-F | n-Pr |
| $CH_2$ | 4-$OCF_3$ | 3-F | i-Pr |
| $CH_2$ | 4-$OCF_3$ | 3-F | n-Bu |
| $CH_2$ | 4-$OCF_3$ | 3-F | i-Bu |
| $CH_2$ | 4-$OCF_3$ | 3-F | c-Pr |
| $CH_2$ | 4-$OCF_3$ | 3-F | Ph |
| $CH_2$ | 4-$OCF_3$ | 3-F | 4-Cl—Ph |
| $CH_2$ | 4-$OCF_3$ | 3-F | 4-F—Ph |
| $CH_2$ | 4-$OCF_3$ | 3-F | 4-CN—Ph |
| $CH_2$ | 4-$OCF_3$ | 3-F | $CO_2Me$ |
| $CH_2$ | 4-$OCF_3$ | 3-Cl | Me |
| $CH_2$ | 4-$OCF_3$ | 3-Cl | Et |
| $CH_2$ | 4-$OCF_3$ | 3-Cl | n-Pr |

TABLE 2-continued

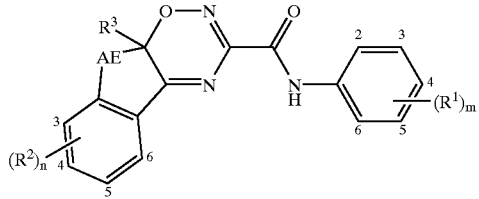

when AE is listed as H, H, there is no link between the rings at AE

| AE | $(R^1)_m$ | $(R^2)_n$ | $R^3$ |
|---|---|---|---|
| CH$_2$ | 4-OCF$_3$ | 3-Cl | i-Pr |
| CH$_2$ | 4-OCF$_3$ | 3-Cl | n-Bu |
| CH$_2$ | 4-OCF$_3$ | 3-Cl | i-Bu |
| CH$_2$ | 4-OCF$_3$ | 3-Cl | c-Pr |
| CH$_2$ | 4-OCF$_3$ | 3-Cl | Ph |
| CH$_2$ | 4-OCF$_3$ | 3-Cl | 4-Cl—Ph |
| CH$_2$ | 4-OCF$_3$ | 3-Cl | 4-F—Ph |
| CH$_2$ | 4-OCF$_3$ | 3-Cl | 4-CN—Ph |
| CH$_2$ | 4-OCF$_3$ | 3-Cl | CO$_2$Me |
| CH$_2$ | 4-OCF$_3$ | 4-Br | Me |
| CH$_2$ | 4-OCF$_3$ | 4-Br | Et |
| CH$_2$ | 4-OCF$_3$ | 4-Br | n-Pr |
| CH$_2$ | 4-OCF$_3$ | 4-Br | i-Pr |
| CH$_2$ | 4-OCF$_3$ | 4-Br | n-Bu |
| CH$_2$ | 4-OCF$_3$ | 4-Br | i-Bu |
| CH$_2$ | 4-OCF$_3$ | 4-Br | c-Pr |
| CH$_2$ | 4-OCF$_3$ | 4-Br | Ph |
| CH$_2$ | 4-OCF$_3$ | 4-Br | 4-Cl—Ph |
| CH$_2$ | 4-OCF$_3$ | 4-Br | 4-F—Ph |
| CH$_2$ | 4-OCF$_3$ | 4-Br | 4-CN—Ph |
| CH$_2$ | 4-OCF$_3$ | 4-Br | CO$_2$Me |
| O | 4-OCF$_3$ | 4-Cl | Me |
| O | 4-OCF$_3$ | 4-Cl | Et |
| O | 4-OCF$_3$ | 4-Cl | n-Pr |
| O | 4-OCF$_3$ | 4-Cl | i-Pr |
| O | 4-OCF$_3$ | 4-Cl | n-Bu |
| O | 4-OCF$_3$ | 4-Cl | i-Bu |
| O | 4-OCF$_3$ | 4-Cl | c-Pr |
| O | 4-OCF$_3$ | 4-Cl | Ph |
| O | 4-OCF$_3$ | 4-Cl | 4-Cl—Ph |
| O | 4-OCF$_3$ | 4-Cl | 4-F—Ph |
| O | 4-OCF$_3$ | 4-Cl | 4-CN—Ph |
| O | 4-OCF$_3$ | 4-Cl | CO$_2$Me |
| O | 4-CF$_3$ | 4-Cl | Me |
| O | 4-CF$_3$ | 4-Cl | Et |
| O | 4-CF$_3$ | 4-Cl | n-Pr |
| O | 4-CF$_3$ | 4-Cl | i-Pr |
| O | 4-CF$_3$ | 4-Cl | n-Bu |
| O | 4-CF$_3$ | 4-Cl | i-Bu |
| O | 4-CF$_3$ | 4-Cl | c-Pr |
| O | 4-CF$_3$ | 4-Cl | Ph |
| O | 4-CF$_3$ | 4-Cl | 4-Cl—Ph |
| O | 4-CF$_3$ | 4-Cl | 4-F—Ph |
| O | 4-CF$_3$ | 4-Cl | 4-CN—Ph |
| O | 4-CF$_3$ | 4-Cl | CO$_2$Me |
| O | 4-OCF$_3$ | 4-CF$_3$ | Me |
| O | 4-OCF$_3$ | 4-CF$_3$ | Et |
| O | 4-OCF$_3$ | 4-CF$_3$ | n-Pr |
| O | 4-OCF$_3$ | 4-CF$_3$ | i-Pr |
| O | 4-OCF$_3$ | 4-CF$_3$ | n-Bu |
| O | 4-OCF$_3$ | 4-CF$_3$ | i-Bu |
| O | 4-OCF$_3$ | 4-CF$_3$ | c-Pr |
| O | 4-OCF$_3$ | 4-CF$_3$ | Ph |
| O | 4-OCF$_3$ | 4-CF$_3$ | 4-Cl—Ph |
| O | 4-OCF$_3$ | 4-CF$_3$ | 4-F—Ph |
| O | 4-OCF$_3$ | 4-CF$_3$ | 4-CN—Ph |
| O | 4-OCF$_3$ | 4-CF$_3$ | CO$_2$Me |
| O | 4-CF$_3$ | 4-CF$_3$ | Me |
| O | 4-CF$_3$ | 4-CF$_3$ | Et |
| O | 4-CF$_3$ | 4-CF$_3$ | n-Pr |
| O | 4-CF$_3$ | 4-CF$_3$ | i-Pr |
| O | 4-CF$_3$ | 4-CF$_3$ | n-Bu |
| O | 4-CF$_3$ | 4-CF$_3$ | i-Bu |
| O | 4-CF$_3$ | 4-CF$_3$ | c-Pr |
| O | 4-CF$_3$ | 4-CF$_3$ | Ph |

TABLE 2-continued

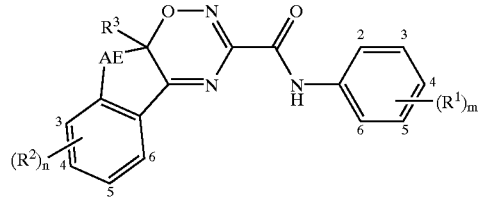

when AE is listed as H, H, there is no link between the rings at AE

| AE | $(R^1)_m$ | $(R^2)_n$ | $R^3$ |
|---|---|---|---|
| O | 4-CF$_3$ | 4-CF$_3$ | 4-Cl—Ph |
| O | 4-CF$_3$ | 4-CF$_3$ | 4-F—Ph |
| O | 4-CF$_3$ | 4-CF$_3$ | 4-CN—Ph |
| O | 4-CF$_3$ | 4-CF$_3$ | CO$_2$Me |
| CH$_2$ | 4-OCF$_3$ | 4-CF$_3$ | Me |
| CH$_2$ | 4-OCF$_3$ | 4-CF$_3$ | Et |
| H, H | 4-OCF$_3$ | 5-CF$_3$ | n-Pr |
| H, H | 4-OCF$_3$ | 5-CF$_3$ | i-Pr |
| H, H | 4-OCF$_3$ | 5-CF$_3$ | n-Bu |
| H, H | 4-OCF$_3$ | 5-CF$_3$ | i-Bu |
| H, H | 4-OCF$_3$ | 5-CF$_3$ | c-Pr |
| H, H | 4-OCF$_3$ | 5-CF$_3$ | Ph |
| H, H | 4-OCF$_3$ | 5-CF$_3$ | 4-Cl—Ph |
| H, H | 4-OCF$_3$ | 5-CF$_3$ | 4-F—Ph |
| H, H | 4-OCF$_3$ | 5-CF$_3$ | 4-CN—Ph |
| H, H | 4-OCF$_3$ | 5-CF$_3$ | CO$_2$Me |
| H, H | 4-CF$_3$ | 5-CF$_3$ | Me |
| H, H | 4-CF$_3$ | 5-CF$_3$ | Et |
| H, H | 4-CF$_3$ | 5-CF$_3$ | n-Pr |
| H, H | 4-CF$_3$ | 5-CF$_3$ | i-Pr |
| H, H | 4-CF$_3$ | 5-CF$_3$ | n-Bu |
| H, H | 4-CF$_3$ | 5-CF$_3$ | i-Bu |
| H, H | 4-CF$_3$ | 5-CF$_3$ | c-Pr |
| H, H | 4-CF$_3$ | 5-CF$_3$ | Ph |
| H, H | 4-CF$_3$ | 5-CF$_3$ | 4-Cl—Ph |
| H, H | 4-CF$_3$ | 5-CF$_3$ | 4-F—Ph |
| H, H | 4-CF$_3$ | 5-CF$_3$ | 4-CN—Ph |
| H, H | 4-CF$_3$ | 5-CF$_3$ | CO$_2$Me |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-CF$_3$ | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-OCF$_3$ | 4-Cl | n-Pr |
| CH$_2$ | 4-Br | 4-Cl | Me |

TABLE 2-continued

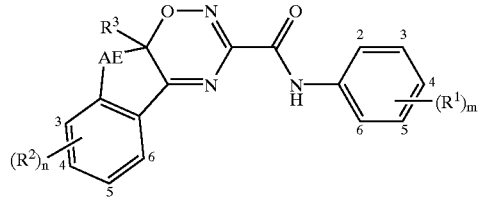

when AE is listed as H, H, there is no link between the rings at AE

| AE | (R¹)ₘ | (R²)ₙ | R³ |
|---|---|---|---|
| CH₂ | 4-Br | 4-Cl | Et |
| CH₂ | 4-Br | 4-Cl | n-Pr |
| CH₂ | 4-Br | 4-Cl | i-Pr |
| CH₂ | 4-Br | 4-Cl | n-Bu |
| CH₂ | 4-Br | 4-Cl | i-Bu |
| CH₂ | 4-Br | 4-Cl | c-Pr |
| CH₂ | 4-Br | 4-Cl | Ph |
| CH₂ | 4-Br | 4-Cl | 4-Cl—Ph |
| CH₂ | 4-Br | 4-Cl | 4-F—Ph |
| CH₂ | 4-Br | 4-Cl | 4-CN—Ph |
| CH₂ | 4-Br | 4-Cl | CO₂Me |
| OCH₂ | 4-OCF₃ | 3-Cl | n-Pr |
| CH₂O | 4-OCF₃ | 3-Cl | n-Pr |
| S | 4-OCF₃ | 4-Cl | n-Pr |
| NH | 4-OCF₃ | 4-Cl | n-Pr |
| CH₂CH₂ | 4-OCF₃ | 3-Cl | n-Pr |
| NHCH₂ | 4-OCF₃ | 3-Cl | n-Pr |
| CH₂NH | 4-OCF₃ | 3-Cl | n-Pr |

TABLE 3

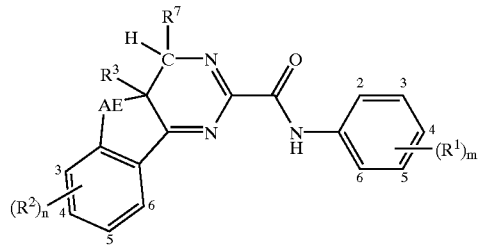

when AE is listed as H, H, there is no link between the rings at AE

| AE | (R¹)ₘ | (R²)ₙ | R³ | R⁶ |
|---|---|---|---|---|
| CH₂ | 4-OCF₃ | 4-Cl | Me | H |
| CH₂ | 4-OCF₃ | 4-Cl | Et | H |
| CH₂ | 4-OCF₃ | 4-Cl | n-Pr | H |
| CH₂ | 4-OCF₃ | 4-Cl | i-Pr | H |
| CH₂ | 4-OCF₃ | 4-Cl | n-Bu | H |
| CH₂ | 4-OCF₃ | 4-Cl | i-Bu | H |
| CH₂ | 4-OCF₃ | 4-Cl | c-Pr | H |
| CH₂ | 4-OCF₃ | 4-Cl | Ph | H |
| CH₂ | 4-OCF₃ | 4-Cl | 4-Cl—Ph | H |
| CH₂ | 4-OCF₃ | 4-Cl | 4-F—Ph | H |
| CH₂ | 4-OCF₃ | 4-Cl | 4-CN—Ph | H |
| CH₂ | 4-OCF₃ | 4-Cl | CO₂Me | H |
| CH₂ | 4-CF₃ | 4-Cl | Me | H |
| CH₂ | 4-CF₃ | 4-Cl | Et | H |
| CH₂ | 4-CF₃ | 4-Cl | n-Pr | H |
| CH₂ | 4-CF₃ | 4-Cl | i-Pr | H |
| CH₂ | 4-CF₃ | 4-Cl | n-Bu | H |
| CH₂ | 4-CF₃ | 4-Cl | i-Bu | H |
| CH₂ | 4-CF₃ | 4-Cl | c-Pr | H |
| CH₂ | 4-CF₃ | 4-Cl | Ph | H |
| CH₂ | 4-CF₃ | 4-Cl | 4-Cl—Ph | H |
| CH₂ | 4-CF₃ | 4-Cl | 4-F—Ph | H |
| CH₂ | 4-CF₃ | 4-Cl | 4-CN—Ph | H |
| CH₂ | 4-CF₃ | 4-Cl | CO₂Me | H |
| CH₂ | 4-OCF₃ | 4-CF₃ | Me | H |
| CH₂ | 4-OCF₃ | 4-CF₃ | Et | H |

TABLE 3-continued

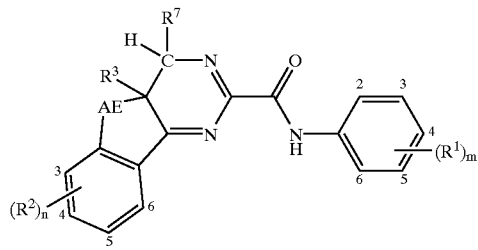

when AE is listed as H, H, there is no link between the rings at AE

| AE | (R¹)ₘ | (R²)ₙ | R³ | R⁶ |
|---|---|---|---|---|
| CH₂ | 4-OCF₃ | 4-CF₃ | n-Pr | H |
| CH₂ | 4-OCF₃ | 4-CF₃ | i-Pr | H |
| CH₂ | 4-OCF₃ | 4-CF₃ | n-Bu | H |
| CH₂ | 4-OCF₃ | 4-CF₃ | i-Bu | H |
| CH₂ | 4-OCF₃ | 4-CF₃ | c-Pr | H |
| CH₂ | 4-OCF₃ | 4-CF₃ | Ph | H |
| CH₂ | 4-OCF₃ | 4-CF₃ | 4-Cl—Ph | H |
| CH₂ | 4-OCF₃ | 4-CF₃ | 4-F—Ph | H |
| CH₂ | 4-OCF₃ | 4-CF₃ | 4-CN—Ph | H |
| CH₂ | 4-OCF₃ | 4-CF₃ | CO₂Me | H |
| CH₂ | 4-CF₃ | 4-CF₃ | Me | H |
| CH₂ | 4-CF₃ | 4-CF₃ | Et | H |
| CH₂ | 4-CF₃ | 4-CF₃ | n-Pr | H |
| CH₂ | 4-CF₃ | 4-CF₃ | i-Pr | H |
| CH₂ | 4-CF₃ | 4-CF₃ | n-Bu | H |
| CH₂ | 4-CF₃ | 4-CF₃ | i-Bu | H |
| CH₂ | 4-CF₃ | 4-CF₃ | c-Pr | H |
| CH₂ | 4-CF₃ | 4-CF₃ | Ph | H |
| CH₂ | 4-CF₃ | 4-CF₃ | 4-Cl—Ph | H |
| CH₂ | 4-CF₃ | 4-CF₃ | 4-F—Ph | H |
| CH₂ | 4-CF₃ | 4-CF₃ | 4-CN—Ph | H |
| CH₂ | 4-CF₃ | 4-CF₃ | CO₂Me | H |
| CH₂ | 4-OCF₃ | 4-F | Me | H |
| CH₂ | 4-OCF₃ | 4-F | Et | H |
| CH₂ | 4-OCF₃ | 4-F | n-Pr | H |
| CH₂ | 4-OCF₃ | 4-F | i-Pr | H |
| CH₂ | 4-OCF₃ | 4-F | n-Bu | H |
| CH₂ | 4-OCF₃ | 4-F | i-Bu | H |
| CH₂ | 4-OCF₃ | 4-F | c-Pr | H |
| CH₂ | 4-OCF₃ | 4-F | Ph | H |
| CH₂ | 4-OCF₃ | 4-F | 4-Cl—Ph | H |
| CH₂ | 4-OCF₃ | 4-F | 4-F—Ph | H |
| CH₂ | 4-OCF₃ | 4-F | 4-CN—Ph | H |
| CH₂ | 4-OCF₃ | 4-F | CO₂Me | H |
| CH₂ | 4-OCF₃ | 3-F | Me | H |
| CH₂ | 4-OCF₃ | 3-F | Et | H |
| CH₂ | 4-OCF₃ | 3-F | n-Pr | H |
| CH₂ | 4-OCF₃ | 3-F | i-Pr | H |
| CH₂ | 4-OCF₃ | 3-F | n-Bu | H |
| CH₂ | 4-OCF₃ | 3-F | i-Bu | H |
| CH₂ | 4-OCF₃ | 3-F | c-Pr | H |
| CH₂ | 4-OCF₃ | 3-F | Ph | H |
| CH₂ | 4-OCF₃ | 3-F | 4-Cl—Ph | H |
| CH₂ | 4-OCF₃ | 3-F | 4-F—Ph | H |
| CH₂ | 4-OCF₃ | 3-F | 4-CN—Ph | H |
| CH₂ | 4-OCF₃ | 3-F | CO₂Me | H |
| CH₂ | 4-OCF₃ | 3-Cl | Me | H |
| CH₂ | 4-OCF₃ | 3-Cl | Et | H |
| CH₂ | 4-OCF₃ | 3-Cl | n-Pr | H |
| CH₂ | 4-OCF₃ | 3-Cl | i-Pr | H |
| CH₂ | 4-OCF₃ | 3-Cl | n-Bu | H |
| CH₂ | 4-OCF₃ | 3-Cl | i-Bu | H |
| CH₂ | 4-OCF₃ | 3-Cl | c-Pr | H |
| CH₂ | 4-OCF₃ | 3-Cl | Ph | H |
| CH₂ | 4-OCF₃ | 3-Cl | 4-Cl—Ph | H |
| CH₂ | 4-OCF₃ | 3-Cl | 4-F—Ph | H |
| CH₂ | 4-OCF₃ | 3-Cl | 4-CN—Ph | H |
| CH₂ | 4-OCF₃ | 3-Cl | CO₂Me | H |
| CH₂ | 4-OCF₃ | 4-Br | Me | H |
| CH₂ | 4-OCF₃ | 4-Br | Et | H |
| CH₂ | 4-OCF₃ | 4-Br | n-Pr | H |
| CH₂ | 4-OCF₃ | 4-Br | i-Pr | H |
| CH₂ | 4-OCF₃ | 4-Br | n-Bu | H |

TABLE 3-continued

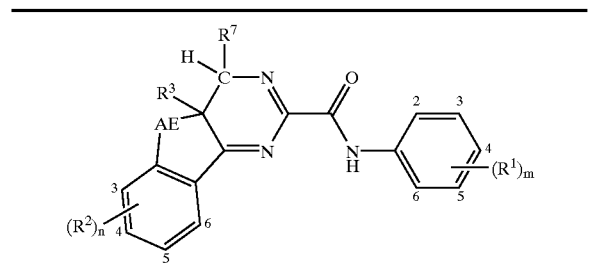

when AE is listed as H, H, there is no link between the rings at AE

| AE | (R¹)ₘ | (R²)ₙ | R³ | R⁶ |
|---|---|---|---|---|
| CH₂ | 4-OCF₃ | 4-Br | i-Bu | H |
| CH₂ | 4-OCF₃ | 4-Br | c-Pr | H |
| CH₂ | 4-OCF₃ | 4-Br | Ph | H |
| CH₂ | 4-OCF₃ | 4-Br | 4-Cl—Ph | H |
| CH₂ | 4-OCF₃ | 4-Br | 4-F—Ph | H |
| CH₂ | 4-OCF₃ | 4-Br | 4-CN—Ph | H |
| CH₂ | 4-OCF₃ | 4-Br | CO₂Me | H |
| O | 4-OCF₃ | 4-Cl | Me | H |
| O | 4-OCF₃ | 4-Cl | Et | H |
| O | 4-OCF₃ | 4-Cl | n-Pr | H |
| O | 4-OCF₃ | 4-Cl | i-Pr | H |
| O | 4-OCF₃ | 4-Cl | n-Bu | H |
| O | 4-OCF₃ | 4-Cl | i-Bu | H |
| O | 4-OCF₃ | 4-Cl | c-Pr | H |
| O | 4-OCF₃ | 4-Cl | Ph | H |
| O | 4-OCF₃ | 4-Cl | 4-Cl—Ph | H |
| O | 4-OCF₃ | 4-Cl | 4-F—Ph | H |
| O | 4-OCF₃ | 4-Cl | 4-CN—Ph | H |
| O | 4-OCF₃ | 4-Cl | CO₂Me | H |
| O | 4-CF₃ | 4-Cl | Me | H |
| O | 4-CF₃ | 4-Cl | Et | H |
| O | 4-CF₃ | 4-Cl | n-Pr | H |
| O | 4-CF₃ | 4-Cl | i-Pr | H |
| O | 4-CF₃ | 4-Cl | n-Bu | H |
| O | 4-CF₃ | 4-Cl | i-Bu | H |
| O | 4-CF₃ | 4-Cl | c-Pr | H |
| O | 4-CF₃ | 4-Cl | Ph | H |
| O | 4-CF₃ | 4-Cl | 4-Cl—Ph | H |
| O | 4-CF₃ | 4-Cl | 4-F—Ph | H |
| O | 4-CF₃ | 4-Cl | 4-CN—Ph | H |
| O | 4-CF₃ | 4-Cl | CO₂Me | H |
| O | 4-OCF₃ | 4-CF₃ | Me | H |
| O | 4-OCF₃ | 4-CF₃ | Et | H |
| O | 4-OCF₃ | 4-CF₃ | n-Pr | H |
| O | 4-OCF₃ | 4-CF₃ | i-Pr | H |
| O | 4-OCF₃ | 4-CF₃ | n-Bu | H |
| O | 4-OCF₃ | 4-CF₃ | i-Bu | H |
| O | 4-OCF₃ | 4-CF₃ | c-Pr | H |
| O | 4-OCF₃ | 4-CF₃ | Ph | H |
| O | 4-OCF₃ | 4-CF₃ | 4-Cl—Ph | H |
| O | 4-OCF₃ | 4-CF₃ | 4-F—Ph | H |
| O | 4-OCF₃ | 4-CF₃ | 4-CN—Ph | H |
| O | 4-OCF₃ | 4-CF₃ | CO₂Me | H |
| O | 4-CF₃ | 4-CF₃ | Me | H |
| O | 4-CF₃ | 4-CF₃ | Et | H |
| O | 4-CF₃ | 4-CF₃ | n-Pr | H |
| O | 4-CF₃ | 4-CF₃ | i-Pr | H |
| O | 4-CF₃ | 4-CF₃ | n-Bu | H |
| O | 4-CF₃ | 4-CF₃ | i-Bu | H |
| O | 4-CF₃ | 4-CF₃ | c-Pr | H |
| O | 4-CF₃ | 4-CF₃ | Ph | H |
| O | 4-CF₃ | 4-CF₃ | 4-Cl—Ph | H |
| O | 4-CF₃ | 4-CF₃ | 4-F—Ph | H |
| O | 4-CF₃ | 4-CF₃ | 4-CN—Ph | H |
| O | 4-CF₃ | 4-CF₃ | CO₂Me | H |
| CH₂ | 4-OCF₃ | 4-CF₃ | Me | H |
| CH₂ | 4-OCF₃ | 4-CF₃ | Et | H |
| H, H | 4-OCF₃ | 5-CF₃ | n-Pr | H |
| H, H | 4-OCF₃ | 5-CF₃ | i-Pr | H |
| H, H | 4-OCF₃ | 5-CF₃ | n-Bu | H |
| H, H | 4-OCF₃ | 5-CF₃ | i-Bu | H |
| H, H | 4-OCF₃ | 5-CF₃ | c-Pr | H |
| H, H | 4-OCF₃ | 5-CF₃ | Ph | H |
| H, H | 4-OCF₃ | 5-CF₃ | 4-Cl—Ph | H |
| H, H | 4-OCF₃ | 5-CF₃ | 4-F—Ph | H |
| H, H | 4-OCF₃ | 5-CF₃ | 4-CN—Ph | H |
| H, H | 4-OCF₃ | 5-CF₃ | CO₂Me | H |
| H, H | 4-CF₃ | 5-CF₃ | Me | H |
| H, H | 4-CF₃ | 5-CF₃ | Et | H |
| H, H | 4-CF₃ | 5-CF₃ | n-Pr | H |
| H, H | 4-CF₃ | 5-CF₃ | i-Pr | H |
| H, H | 4-CF₃ | 5-CF₃ | n-Ru | H |
| H, H | 4-CF₃ | 5-CF₃ | i-Bu | H |
| H, H | 4-CF₃ | 5-CF₃ | c-Pr | H |
| H, H | 4-CF₃ | 5-CF₃ | Ph | H |
| H, H | 4-CF₃ | 5-CF₃ | 4-Cl—Ph | H |
| H, H | 4-CF₃ | 5-CF₃ | 4-F—Ph | H |
| H, H | 4-CF₃ | 5-CF₃ | 4-CN—Ph | H |
| H, H | 4-CF₃ | 5-CF₃ | CO₂Me | H |
| CH₂ | 4-OCF₃ | 4-CF₃ | n-Pr | Me |
| CH₂ | 4-OCF₃ | 4-CF₃ | n-Pr | Et |
| CH₂ | 4-OCF₃ | 4-CF₃ | n-Pr | n-Pr |
| CH₂ | 4-OCF₃ | 4-CF₃ | n-Pr | i-Pr |
| CH₂ | 4-OCF₃ | 4-CF₃ | n-Pr | n-Bu |
| CH₂ | 4-OCF₃ | 4-CF₃ | n-Pr | s-Bu |
| CH₂ | 4-OCF₃ | 4-CF₃ | n-Pr | i-Bu |
| CH₂ | 4-OCF₃ | 4-Cl | n-Pr | Me |
| CH₂ | 4-OCF₃ | 4-Cl | n-Pr | Et |
| CH₂ | 4-OCF₃ | 4-Cl | n-Pr | n-Pr |
| CH₂ | 4-OCF₃ | 4-Cl | n-Pr | i-Pr |
| CH₂ | 4-OCF₃ | 4-Cl | n-Pr | n-Ru |
| CH₂ | 4-OCF₃ | 4-Cl | n-Pr | s-Bu |
| CH₂ | 4-OCF₃ | 4-Cl | n-Pr | i-Bu |
| CH₂ | 4-Br | 4-Cl | Me | H |
| CH₂ | 4-Br | 4-Cl | Et | H |
| CH₂ | 4-Br | 4-Cl | n-Pr | H |
| CH₂ | 4-Br | 4-Cl | i-Pr | H |
| CH₂ | 4-Br | 4-Cl | n-Bu | H |
| CH₂ | 4-Br | 4-Cl | i-Bu | H |
| CH₂ | 4-Br | 4-Cl | c-Pr | H |
| CH₂ | 4-Br | 4-Cl | Ph | H |
| CH₂ | 4-Br | 4-Cl | 4-Cl—Ph | H |
| CH₂ | 4-Br | 4-Cl | 4-F—Ph | H |
| CH₂ | 4-Br | 4-Cl | 4-CN—Ph | H |
| CH₂ | 4-Br | 4-Cl | CO₂Me | H |
| OCH₂ | 4-OCF₃ | 3-Cl | n-Pr | H |
| CH₂O | 4-OCF₃ | 3-Cl | n-Pr | H |
| S | 4-OCF₃ | 4-Cl | n-Pr | H |
| NH | 4-OCF₃ | 4-Cl | n-Pr | H |
| CH₂CH₂ | 4-OCF₃ | 3-Cl | n-Pr | H |
| NHCH₂ | 4-OCF₃ | 3-Cl | n-Pr | H |
| CH₂NH | 4-OCF₃ | 3-Cl | n-Pr | H |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

Example A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 1 | 10.0% |
| attapulgite granules (low volatile matter, 0.71/0.30 mm; U.S.S. No. 25–50 sieves) | 90.0%. |

Example C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), green peach aphid (*Myzus persica*), cotton aphid (*Aphis gossypii*), Russian wheat aphid (*Diuraphis noxia*), English grain aphid (*Sitobion avenae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae, Tetranychus cinnabarinus, Tetranychus mcdanieli, Tetranychus pacificus, Tetranychus turkestani, Byrobia rubrioculus, Panonychus ulmi, Panonychus citri, Eotetranychus carpini borealis, Eotetranychus, hicoriae, Eotetranychus sexmaculatus, Eotetranychus yumensis, Eotetranychus banksi* and *Oligonychus pratensis*; Tenuipalpidae including *Brevipalpus lewisi, Brevipalpus phoenicis, Brevipalpus californicus* and *Brevipalpus obovatus*; Eriophyidae including *Phyllocoptruta oleivora, Eriophyes sheldoni, Aculus cornutus, Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-Chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as acibenzolar, azoxystrobin, binomial, blasticidin-S, Bordeaux mixture (Triassic copper sulfate), bromuconazole, capropamid (KTU 3616), captafol, captan, carbendazim, chloroneb, chlorothalonil, copper oxychloride, copper salts, cymoxanil, cyproconazole, cyprodinil (CGA 219417), (S)-3,5-dichloro-N-(3-Chloro-1-ethyl-1-methyl-2-oxopropyl)-4-methylbenzamide (RH 7281), diclocymet (S-2900), diclomezine, dicloran, difenoconazole,(S)-3,5-dihydro-5-methyl-2-(methylthio)-5-phenyl-3-(phenylamino)-4H-imidazol-4-one (RP 407213), dimethomorph, diniconazole, diniconazole-M, dodine, edifenphos, epoxiconazole (BAS 480F), famoxadone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothidlane, kasugamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyrimethanil, pyroquilon, quinoxyfen, spiroxamine, sulfur, tebuconazole, tetraconazole, thiabendazole, thifluzamide, thiophanate-methyl, thiram, triadimefon, triadimenol, tricyclazole, triticonazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other arthropodicides having a similar spectrum of control but a different mode of action will be particularly advantageous for resistance management.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of the invention, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyi butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Table A for compound descriptions. The following abbreviations are used in the Index Table that follows: n is normal, i is iso, Pr ispropyl, and Ph is phenyl. The abbreviation "Ex." stands for "Example" and is followed by a number indicating in which example the compound is prepared.

INDEX TABLE A

| Cmpd No. | $(R^1)_m$ | $(R^2)_n$ | $R^3$ | $R^7$ | mp ° C. |
|---|---|---|---|---|---|
| 1 | 4-OCF$_3$ | 4-Cl | n-Pr | H | 167–170 |
| 2 | 4-Br | 4-Cl | n-Pr | H | 185–186 |
| 3 (Ex. 1) | 4-OCF$_3$ | 4-CF$_3$ | n-Pr | H | 192–194 |
| 4 (Ex. 2) | 4-Br | 4-CF$_3$ | n-Pr | H | 198–199 |
| 5 | 4-CF$_3$ | 4-Cl | n-Pr | CH$_3$ | 91–93 |
| 6 | 4-OCF$_3$ | 4-Cl | n-Pr | CH$_3$ | 67–72 |
| 7 | 4-CF$_3$ | 4-CF$_3$ | n-Pr | CH$_3$ | 124–126 |
| 8 | 4-OCF$_3$ | 4-CF$_3$ | n-Pr | CH$_3$ | 75–77 |
| 9 | 4-CF$_3$ | 4-CF$_3$ | CH$_3$ | CH$_3$ | 80–82 |
| 10 | 4-OCF$_3$ | 4-CF$_3$ | CH$_3$ | CH$_3$ | 80–90 |
| 11 | 4-CF$_3$ | 4-CF$_3$ | n-Pr | COCH$_3$ | 182–184 |
| 12 | 4-OCF$_3$ | 4-CF$_3$ | n-Pr | COCH$_3$ | 128–130 |
| 13 | 4-OCF$_3$ | 4-F | 4-FPh | H | 189–191 |
| 14 | 4-OCF$_3$ | 4-F | CH$_3$ | H | 211–212 |
| 15 | 4-OCF$_3$ | 4-Cl | i-Pr | H | 178–179 |
| 16 | 4-OCF$_3$ | 4-F | 4-FPh | CO$_2$CH$_3$ | 104–106 |
| 17 | 4-OCF$_3$ | 4-F | CH$_3$ | CH$_3$ | 169–171 |
| 18 | 4-OCF$_3$ | 4-F | CH$_3$ | CO$_2$CH$_3$ | 83–85 |

INDEX TABLE A-continued

| Cmpd No. | $(R^1)_m$ | $(R^2)_n$ | $R^3$ | $R^7$ | mp ° C. |
|---|---|---|---|---|---|
| 19 | 4-CF$_3$ | 4-F | CH$_3$ | CH$_3$ | 133–134 |
| 20 | 4-SCF$_3$ | 4-Cl | n-Pr | H | 190–191 |
| 21 | 4-SCF$_3$ | 4-CF$_3$ | n-Pr | H | 200–202 |
| 22 | 4-SCF$_3$ | 4-F | 4-FPh | H | 195–196 |
| 23 | 4-SCF$_3$ | 4-F | CH$_3$ | H | 136–138 |
| 24 | 3,4-OCF$_2$O— | 4-Cl | n-Pr | H | 180–181 |
| 25 | 3,4-OCF$_2$O— | 4-CF$_3$ | n-Pr | H | 125–128 |
| 26 | 3,4-OCF$_2$O— | 4-F | CH$_3$ | H | 110–113 |
| 27 | 3,4-OCF$_2$O— | 4-Cl | i-Pr | H | 201–202 |

BIOLOGICAL EXAMPLES OF THE INVENTION TEST A

Fall Armyworm

Test units, each consisting of a H.I.S. (high impact styrene) tray with 16 cells were prepared. Wet filter paper and approximately 8 cm² of lima bean leaf were placed into twelve of the cells. A 0.5-Cm layer of wheat germ diet was placed into the four remaining cells. Fifteen to twenty third-instar larvae of fall armyworm (Spodoptera frugiperda) were placed into a 230-mL (8-ounce) plastic cup. Solutions of each of the test compounds in 75:25 acetone-distilled water solvent were sprayed into the tray and cup. Spraying was accomplished by passing the tray and cup on a conveyer belt directly beneath a flat fan hydraulic nozzle which discharged the spray at a rate of 0.138 kilograms of active ingredient per hectare (about 0.13 pounds per acre) at 207 kPa (30 p.s.i.). The insects were transferred from the 230-mL cup to the H.I.S. tray (one insect per cell). The trays were covered and held at 27° C. and 50% relative humidity for 48 hours, after which time readings were taken on the twelve cells with lima bean leaves. The four remaining cells were read at 6–8 days for delayed toxicity. Of the compounds tested, the following gave control efficacy levels of 80% or greater: 1, 2, 3, 4, 5, 6, 7, 8, 9, 10, 11, 12, 13, 14, 15, 16, 17, 19, 20, 21, 22, 24, 25 and 27.

TEST B

Tobacco Budworm

The test procedure of TEST A was repeated for determining efficacy against third-instar larvae of the tobacco budworm (Heliothis virescens) except that three 230-mL (8-ounce) plastic cups with wheat germ diet were used in place of the H.I.S. tray, with each cup pre-infected with five third-instar larvae. Of the compounds tested, the following gave mortality levels of 80% or higher: 1, 2, 3, 4, 5, 6, 7, 8, 9, 10, 11, 12, 13, 14, 15, 16, 17, 19, 20, 21, 22, 24, 25 and 27.

What is claimed is:

1. A compound selected from Formula I, N-oxides and agriculturally suitable salts thereof,

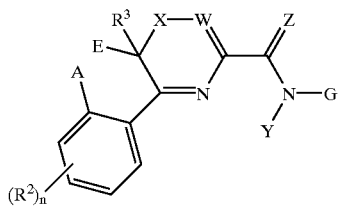

I wherein:

A is H;

E is H or $C_1$–$C_3$ alkyl; or

A and E can be taken together to form —$CH_2$—, —$CH_2CH_2$—, —O—, —S—, —S(O)—, —$S(O)_2$—, —$NR^8$, —$OCH_2$—, —$SCH_2$—, —$N(R^8)CH_2$—, substituted —$CH_2$— and substituted —$CH_2CH_2$—, the substituents independently selected from 1-2 halogen and 1-2 methyl;

G is selected from the group consisting of

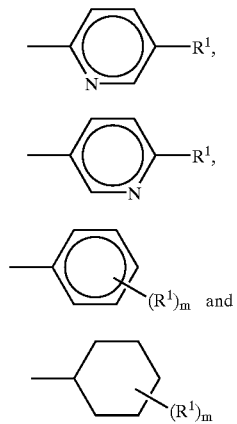

W is N;

X is $NR^7$;

Y is H, $C_1$–$C_6$ alkyl, $C_2$–$C_6$ alkenyl, $C_2$–$C_6$ alkynyl, $C_1$–$C_3$ alkylsulfonyl, $C_3$–$C_6$ cycloalkyl, $C_3$–$C_6$ cycloalkylalkyl, $NR^9R^{10}$, $N=CR^{11}R^{12}$, $OR^7$, $COR^{13}$, $CO_2R^{14}$ or $C_1$–$C_6$ alkyl substituted by at least one group selected from halogen, $C_1$–$C_3$ alkoxy, CN, $NO_2$, $S(O)_rR^{15}$, $COR^{13}$, $CO_2R^{14}$ and optionally substituted phenyl;

Z is O or S;

each $R^1$ and $R^2$ is independently selected from the group consisting of $C_1$–$C_6$ haloalkyl, $C_2$–$C_6$ haloalkenyl, halogen, CN, $NO_2$, $OR^{16}$, $S(O)_rR^{15}$, $OS(O)_2R^{15}$, $CO_2R^{14}$, $C(O)R^{13}$, $C(O)NR^9R^{10}$, $SO_2NR^9R^{10}$, $SF_5$, optionally substituted phenyl and optionally substituted benzyl; or when m or n is 2, $(R^1)_2$ can be taken together or $(R^2)_2$ can be taken together as —$OCH_2O$—, —$OCF_2O$—, —$OCH_2CH_2O$—, —$CH_2C(CH_3)_2O$—, —$CF_2CF_2O$ or —$OCF_2CF_2O$—;

$R^3$ is selected from the group consisting of J, $C(R^{17})=N—O—R^{18}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxyalkyl, $C_3$–$C_8$ alkoxycarbonylalkyl, $CO_2R^{14}$, $C(O)R^{13}$, $C(O)NR^9R^{10}$, $C(S)NR^9R^{10}$, $C(S)R^{13}$, $C(S)SR^{13}$, CN, and optionally substituted phenyl; or $R^3$ is $C_2$–$C_6$ epoxyalkyl optionally substituted with a group selected from $C_1$–$C_3$ alkyl, CN, $C(O)R^{13}$, $CO_2R^{14}$ and optionally substituted phenyl; or $R^3$ is $C_1$–$C_6$ alkyl substituted with a group selected from $C(O)NR^9R^{10}$, $COR^{13}$, $CO_2R^{14}$, $S(O)_mR^{15}$, SCN, CN, $C_1$–$C_2$ haloalkoxy, $SiR^{19}R^{20}R^{21}$, $NR^9R^{10}$, $NO_2$, $OC(O)R^{13}$, —$P(O)(OR^{22})_2$, optionally substituted phenyl, and J;

J is a nonaromatic or aromatic 5- or 6-membered heterocyclic ring, bonded through carbon or nitrogen, containing 1–4 heteroatoms independently selected from the group consisting of 0-2 oxygen, 0-2 sulfur and 0-4 nitrogen, optionally containing one carbonyl moiety and optionally substituted;

each $R^7$ is independently H, $C_1$–$C_4$ alkyl, $C_1$–$C_4$ haloalkyl, $C_2$–$C_4$ alkenyl, $C_2$–$C_4$ alkynyl, $C_1$–$C_4$ alkoxy, $SO_2NR^9R^{10}$, $SO_2R^{13}$, $COR^9$, $CONR^9R^{10}$, $CO_2R^{13}$, optionally substituted phenyl or optionally substituted benzyl;

each $R^8$ is independently H, $C_1$–$C_4$ alkyl, $C_1$–$C_4$ alkoxyalkyl, $CO_2R^{13}$, $SO_2R^{13}$, or optionally substituted benzyl;

each $R^9$ and each $R^{11}$ is independently H, $C_1$–$C_4$ alkyl, $C_1$–$C_4$ haloalkyl or optionally substituted phenyl;

each $R^{10}$ and each $R^{12}$ is independently H or $C_1$–$C_4$ alkyl; or each pair of $R^9$ and $R^{10}$ when attached to the same atom or each pair of $R^{11}$ and $R^{12}$ when attached to the same atom independently can be taken together as —$CH_2CH_2CH_2$—, —$CH_2CH_2CH_2CH_2$—, —$CH_2CH_2CH_2CH_2CH_2$— or —$CH_2CH_2OCH_2CH_2$—, each of which is optionally and independently substituted with 1 or 2 $CH_3$ groups;

each $R^{13}$ and each $R^{15}$ is independently H, $C_1$–$C_4$ alkyl, $C_1$–$C_4$ haloalkyl or optionally substituted phenyl;

each $R^{14}$ is independently H, $C_1$–$C_4$ alkyl, $C_1$–$C_4$ haloalkyl or optionally substituted benzyl;

$R^{16}$ is H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, optionally substituted phenyl and optionally substituted benzyl;

$R^{17}$ is selected from the group consisting of H, Cl, $C_1$–$C_4$ alkyl, $C_1$–$C_4$ alkoxy, $C_1$–$C_2$ thioalkyl and CN;

$R^{18}$ is selected from the group consisting of H, $C_1$–$C_4$ alkyl, $C_2$–$C_3$ alkylcarbonyl and $C_2$–$C_3$ alkoxycarbonyl;

$R^{19}$ and $R^{20}$ are each independently $C_1$–$C_3$ alkyl;

$R^{21}$ is selected from the group consisting of H, $C_1$–$C_3$ alkyl and optionally substituted phenyl;

each $R^{22}$ is independently H or $C_1$–$C_4$ alkyl;

each m and n are independently 1 to 3; and r is 0, 1 or 2.

2. A compound of claim 1 wherein

Y is H, $C_1$–$C_6$ alkyl, $C_2$–$C_6$ alkenyl, $C_2$–$C_6$ alkynyl, $C_1$–$C_3$ alkylsulfonyl, $C_3$–$C_6$ cycloalkyl, $C_3$–$C_6$ cycloalkylalkyl, $NR^9R^{10}$, $N=CR^{11}R^{12}$, $OR^7$, $COR^{13}$, $CO_2R^{14}$ or $C_1$–$C_6$ alkyl substituted by at least one group selected from halogen, $C_1$–$C_3$ alkoxy, CN, $NO_2$, $S(O)_rR^{15}$, $COR^{13}$, $CO_2R^{14}$ and phenyl optionally substituted with $R^{23}$ and $R^{24}$;

each $R^1$ and $R^2$ is independently selected from the group consisting of $C_1$–$C_6$ haloalkyl, $C_2$–$C_6$ haloalkenyl, halogen, CN, $NO_2$, $OR^{16}$, $S(O)_rR^{15}$, $OS(O)_2R^{15}$, $CO_2R^{14}$, $C(O)R^{13}$, $C(O)NR^9R^{10}$, $SO_2NR^9R^{10}$, $SF_5$, phenyl optionally substituted with $R^{23}$ and $R^{24}$ and benzyl optionally substituted with $R^{23}$ and $R^{24}$; or when m or n is 2, $(R^1)_2$ can be taken together or $(R^2)_2$ can be taken together as —$OCH_2O$—, —$OCF_2O$—, —$OCH_2CH_2O$—, —$CH_2C(CH_3)_2$—, —$CF_2CF_2O$ or —$OCF_2CF_2O$—;

$R^3$ is selected from the group consisting of J, $C(R^{17})$=N—O—$R^{18}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxylalkyl, $C_3$–$C_8$ alkoxycarbonylalkyl, $CO_2R^{14}$, $C(O)R^{13}$, $C(O)NR^9R^{10}$, $C(S)NR^9R^{10}$, $C(S)R^{13}$, $C(S)SR^{13}$, CN, and phenyl optionally substituted with $R^{23}$ and $R^{24}$; or $R^3$ is $C_2$–$C_6$ epoxyalkyl optionally substituted with a group selected from $C_1$–$C_3$ alkyl, CN, $C(O)R^{13}$, and $CO_2R^{14}$ and phenyl optionally substituted with $R^{23}$ and $R^{24}$; or $R^3$ is $C_1$–$C_6$ alkyl substituted with a group selected from $C(O)NR^9R^{10}$, $COR^{13}$, $CO_2R^{14}$, $S(O)_mR^{15}$, SCN, CN, $C_1$–$C_2$ haloalkoxy, $SiR^{19}R^{20}R^{21}$, $NR^9R^{10}$, $NO_2$, $OC(O)R^{13}$, —$P(O)(OR^{22})_2$, phenyl optionally substituted with $R^{23}$ and $R^{24}$, and J;

J is a nonaromatic or aromatic 5- or 6-membered heterocyclic ring, bonded through carbon or nitrogen, containing 1–4 heteroatoms independently selected from the group consisting of 0-2 oxygen, 0-2 sulfur and 0-4 nitrogen, optionally containing one carbonyl moiety and optionally substituted with $R^{23}$ and $R^{24}$;

each $R^7$ is independently H, $C_1$–$C_4$ alkyl, $C_1$–$C_4$ haloalkyl, $C_2$–$C_4$ alkenyl, $C_2$–$C_4$ alkynyl, $C_1$–$C_4$ alkoxy, $SO_2NR^9R^{10}$, $SO_2R^{13}$, $COR^9$, $CONR^9R^{10}$, $CO_2R^{13}$, phenyl optionally substituted with $R^{23}$ and $R^{24}$ or benzyl optionally substituted with $R^{23}$ and $R^{24}$;

each $R^8$ is independently H, $C_1$–$C_4$ alkyl, $C_1$–$C_4$ alkoxyalkyl, $CO_2R^{13}$, $SO_2R^{13}$, or benzyl optionally substituted with $R^{23}$ and $R^{24}$;

each $R^9$ and each $R^{11}$ is independently H, $C_1$–$C_4$ alkyl, $C_1$–$C_4$ haloalkyl or phenyl optionally substituted with $R^{23}$ and $R^{24}$;

each $R^{10}$ and each $R^{12}$ is independently H or $C_1$–$C_4$ alkyl; or each pair of $R^9$ and $R^{10}$ when attached to the same atom or each pair of $R^{11}$ and $R^{12}$ when attached to the same atom independently can be taken together as —$CH_2CH_2CH_2$—, —$CH_2CH_2CH_2CH_2$—, —$CH_2CH_2CH_2CH_2CH_2$— or —$CH_2CH_2OCH_2CH_2$—, each of which is optionally and independently substituted with 1 or 2 $CH_3$ groups;

each $R^{13}$ and each $R^{15}$ is independently H, $C_1$–$C_4$ alkyl, $C_1$–$C_4$ haloalkyl or phenyl optionally substituted with $R^{23}$ and $R^{24}$;

each $R^{14}$ is independently H, $C_1$–$C_4$ alkyl, $C_1$–$C_4$ haloalkyl or benzyl optionally substituted with $R^{23}$ and $R^{24}$;

$R^{16}$ is H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with $R^{23}$ and $R^{24}$ and benzyl optionally substituted with $R^{23}$ and $R^{24}$;

$R^{21}$ is selected from the group consisting of H, $C_1$–$C_3$ alkyl and phenyl optionally substituted with $R^{23}$ and $R^{24}$;

each $R^{23}$ is independently selected from the group consisting of 1-2, halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl; and each $R^{24}$ is independently selected from the group consisting of halogen, $C_1$–$C_4$ alkyl, $C_1$–$C_4$ alkoxy, $C_1$–$C_4$ haloalkyl and $C_1$–$C_4$ haloalkoxy.

3. The compound of claim 2 which is 7-Chloro-9,9α-dihydro-9α-propyl-N-[4-(trifluoromethoxy)phenyl]-1H-indeno[1,2-e]-1,2,4-triazine-3-carboxamide.

4. An arthropodicidal composition comprising an arthropodicidally effective amount of a compound of claim 1 and at least one additional component selected from the group consisting of surfactants, solid diluents and liquid diluents.

5. A method for controlling arthropods comprising contacting the arthropods or their environment with an arthropodicidally effective amount of a compound of claim 1.

* * * * *

UNITED STATES PATENT AND TRADEMARK OFFICE
CERTIFICATE OF CORRECTION

PATENT NO.   : 6,818,641 B2
DATED        : November 16, 2004
INVENTOR(S)  : Piotrowski David Walter It is certified that error appears in the above-identified patent and that said Letters Patent is hereby corrected as shown below:

Title page,
Item [56], References Cited, U.S. PATENT DOCUMENTS,
"5,462,938A   10/1995   Annus et al." should be
-- 5,462,938A   10/1995   Annis et al. --.

Column 2,
Line 38, "$S(O)_m R^{15}$" should be -- $S(O)_r R^{15}$ --.

Column 10,
Line 67, "$S(O)_m R^{15}$" should be -- $S(O)_r R^{15}$ --.

Column 37,
Lines 48 and 53, "$S(O)_r R^{15}$" should be -- $S(O)_r R^{15}$ --.

Column 38,
Line 4, "$S(O)_m R^{15}$" should be -- $S(O)_r R^{15}$ --.
Lines 62 and 66, "$S(O)_r R^{15}$" should be -- $S(O)_r R^{15}$ --.

Column 39,
Line 18, "$S(O)_m R^{15}$" should be -- $S(O)_r R^{15}$ --.

Column 40,
Lines 32-34, "7-Chloro-9,9α-dihydro-9α-propyl-N-[4-(trifluoromethoxy)phenyl]-1H-indeno[1,2-e]-1,2,4-triazine-3-carboxamide" should be -- 7-Chloro-9,9α-dihydro-9α-propyl-N-[4-(trifluoromethoxy)phenyl]-1*H*-indeno[1,2-*e*]-1,2,4-triazine-3-carboxamide --.

Signed and Sealed this

Fourth Day of April, 2006

JON W. DUDAS
*Director of the United States Patent and Trademark Office*